United States Patent
Sridhar et al.

(10) Patent No.: US 11,517,754 B2
(45) Date of Patent: Dec. 6, 2022

(54) TREATMENT OF TYPE 1 DIABETES

(71) Applicants: Galvani Bioelectronics Limited, Middlesex (GB); Centre Nationale de La Recherche Scientifique, Paris (FR); Université Côte d'Azur, Nice (FR)

(72) Inventors: Arun Sridhar, Stevenage (GB); Philippe Blancou, Nice (FR); Nicolas Glaichenhaus, Nice (FR)

(73) Assignees: Galvani Bioelectronics Limited, Middlesex (GB); Centre Nationale de La Recherche Scientifique, Paris (FR); Université Côte d'Azur, Nice (FR)

(*) Notice: Subject to any disclaimer, the term of this patent is extended or adjusted under 35 U.S.C. 154(b) by 0 days.

(21) Appl. No.: 16/610,658

(22) PCT Filed: May 4, 2018

(86) PCT No.: PCT/EP2018/061563
§ 371 (c)(1),
(2) Date: Nov. 4, 2019

(87) PCT Pub. No.: WO2018/202877
PCT Pub. Date: Nov. 8, 2018

(65) Prior Publication Data
US 2021/0339025 A1    Nov. 4, 2021

(30) Foreign Application Priority Data
May 5, 2017  (GB) ..................................... 1707207

(51) Int. Cl.
*A61N 1/36*    (2006.01)
*A61N 1/05*    (2006.01)

(52) U.S. Cl.
CPC ....... *A61N 1/36121* (2013.01); *A61N 1/0556* (2013.01); *A61N 1/36057* (2013.01); *A61N 1/36135* (2013.01); *A61N 1/36146* (2013.01)

(58) Field of Classification Search
CPC .............. A61N 1/0556; A61N 1/36057; A61N 1/36121; A61N 1/36135; A61N 1/36146
USPC ............................................................ 607/2
See application file for complete search history.

(56) References Cited

U.S. PATENT DOCUMENTS

| | | |
|---|---|---|
| 8,457,745 B1 | 6/2013 | Garcia et al. |
| 8,504,161 B1 | 8/2013 | Kornet et al. |
| 2005/0075701 A1 | 4/2005 | Shafer |
| 2014/0046407 A1 | 2/2014 | Ben-Ezra et al. |
| 2019/0046795 A1* | 2/2019 | Cakmak .............. A61N 1/36031 |
| 2019/0060546 A1* | 2/2019 | Callaghan ............ A61B 5/6852 |

FOREIGN PATENT DOCUMENTS

| | | |
|---|---|---|
| WO | 2004/021858 A2 | 3/2004 |
| WO | 2006/023498 A1 | 3/2006 |
| WO | 2007/018788 A2 | 2/2007 |
| WO | WO 2007/092330 A1 | 8/2007 |

* cited by examiner

*Primary Examiner* — Carl H Layno
*Assistant Examiner* — Jane C Kalinock
(74) *Attorney, Agent, or Firm* — Banner & Witcoff, Ltd.

(57) ABSTRACT

Modulation of neural signaling of a pancreas-related sympathetic nerve is capable of improving glycaemic control by inhibiting T cell activation or migration to the pancreas, and hence providing a way of treating or preventing type 1 diabetes.

20 Claims, 23 Drawing Sheets

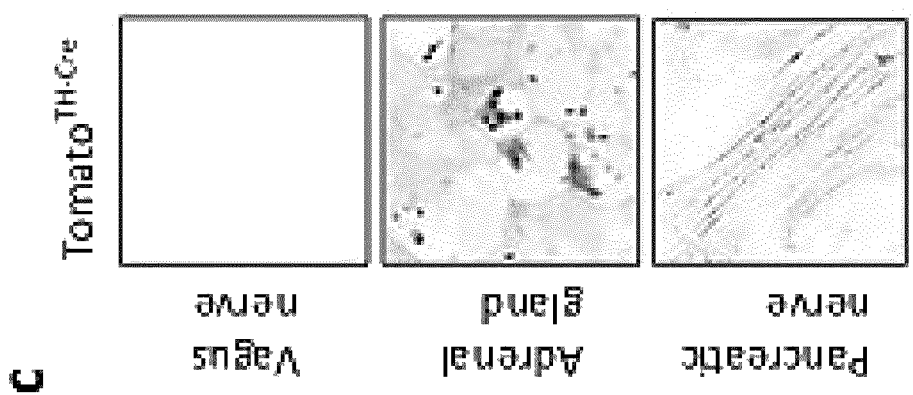
FIG. 1C
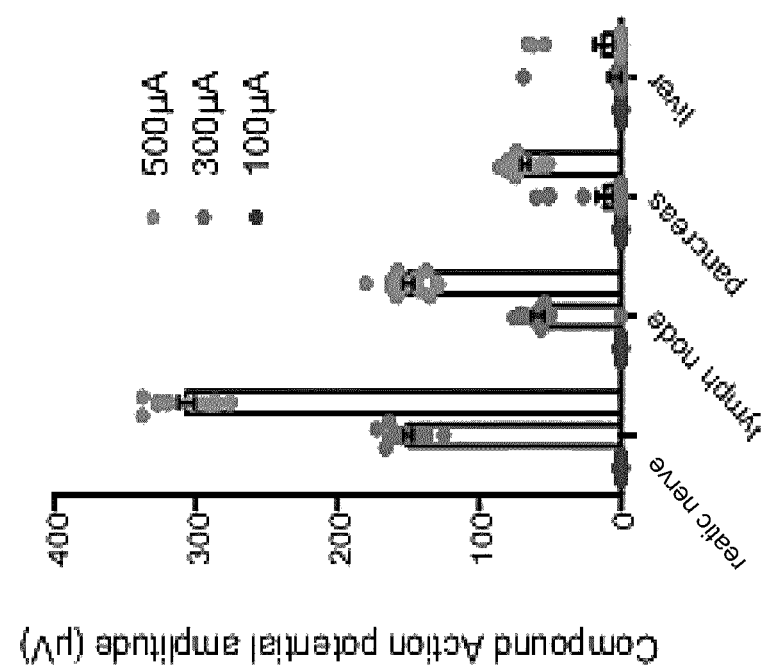
FIG. 1B
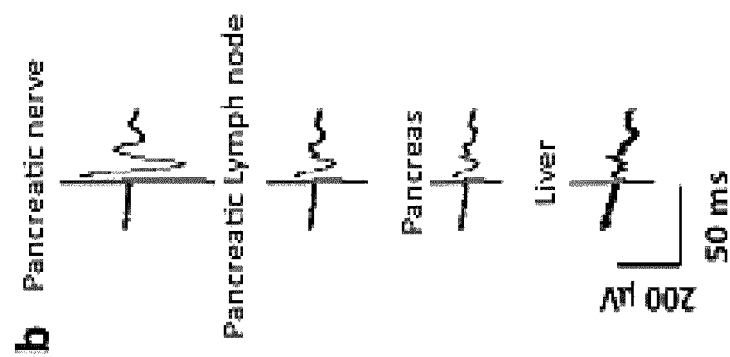

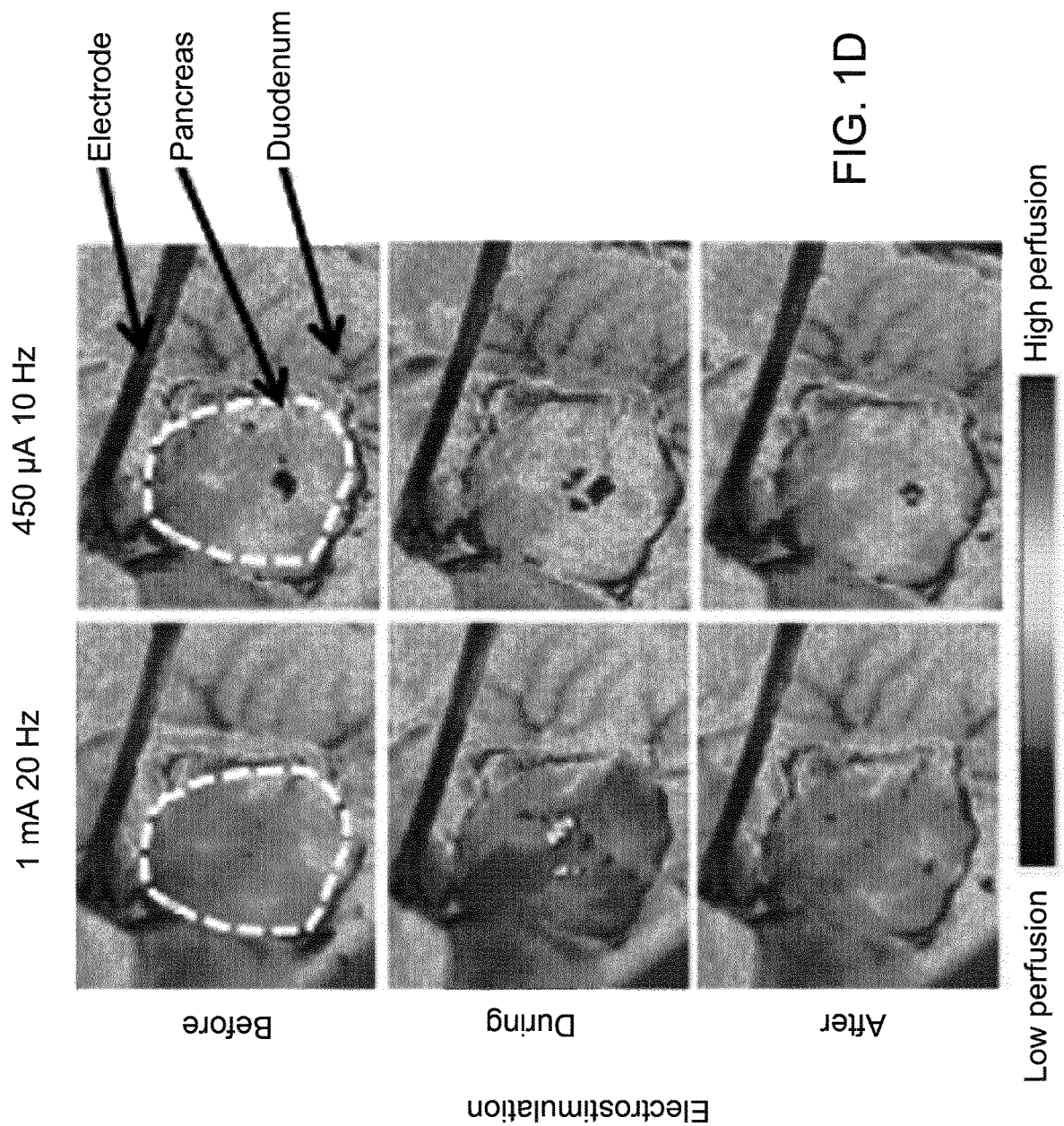

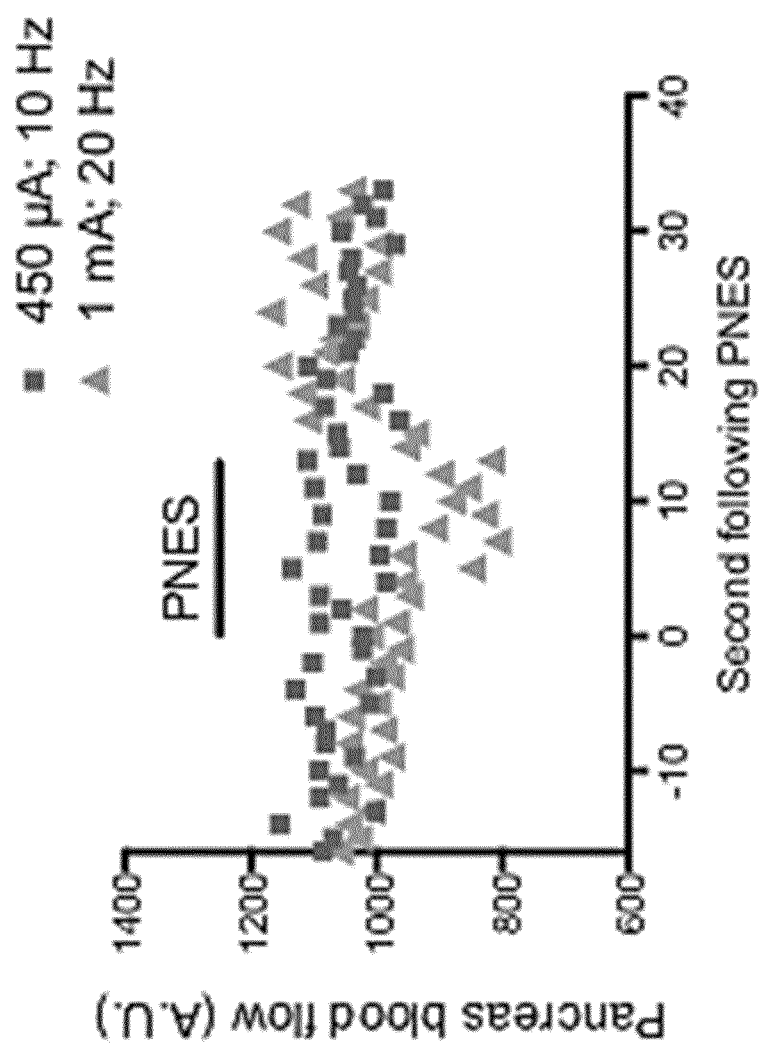

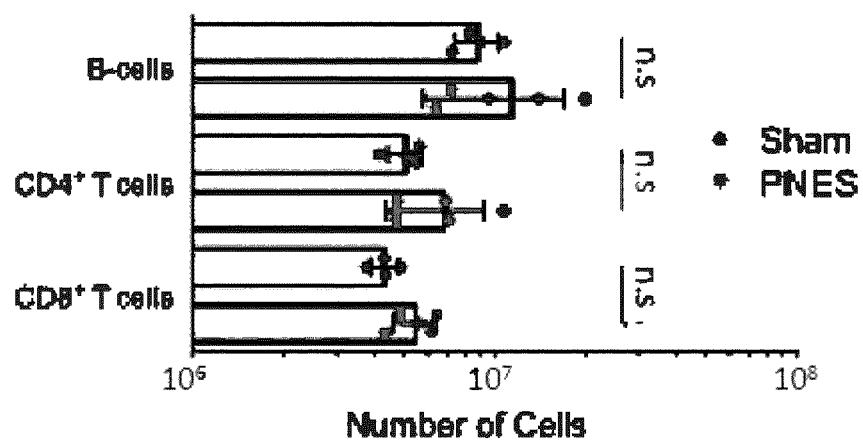
Fig. 3A

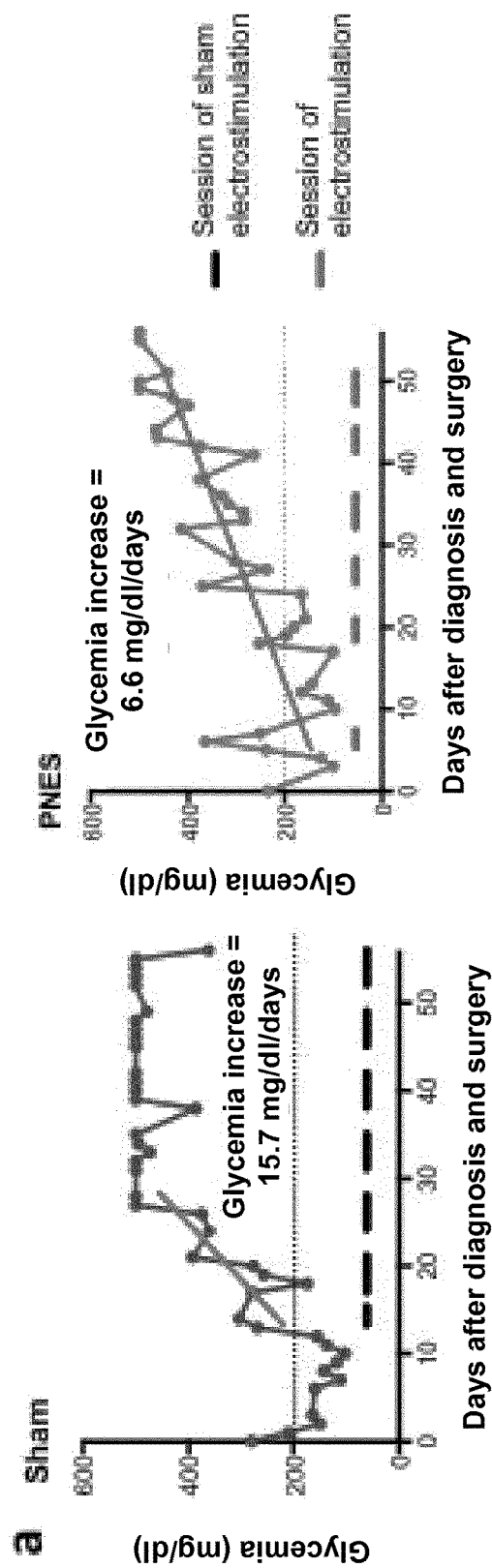
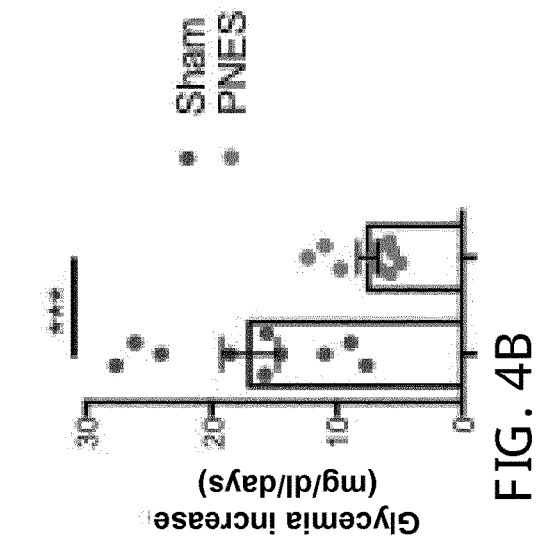
FIG. 4A
FIG. 4B

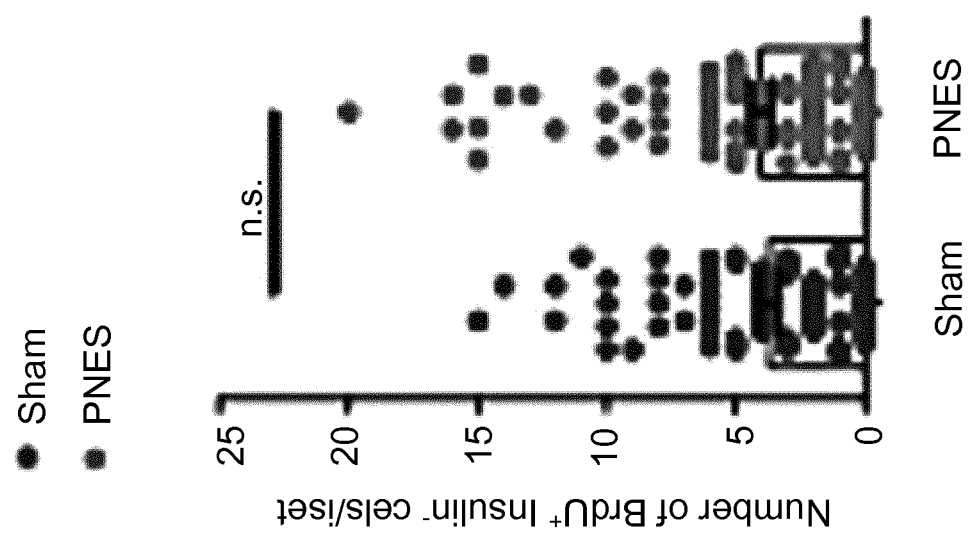
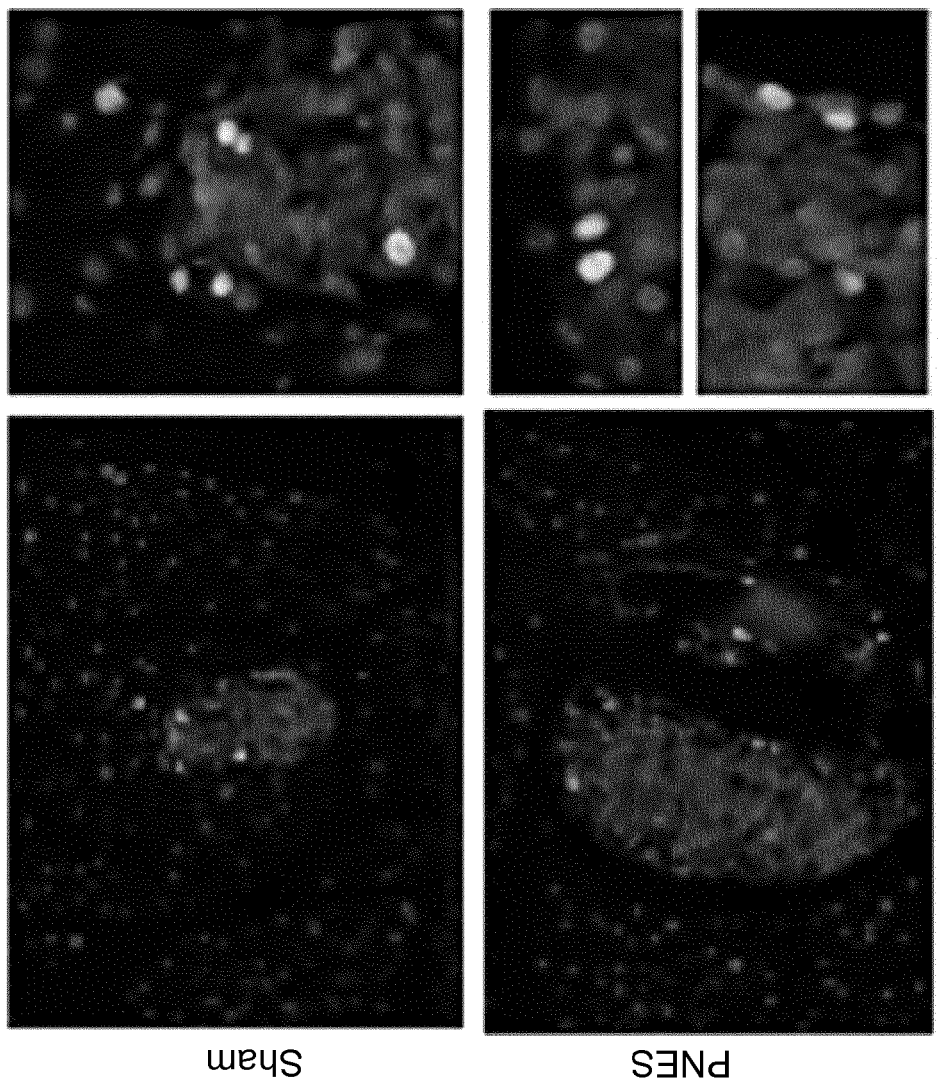
FIG. 4F

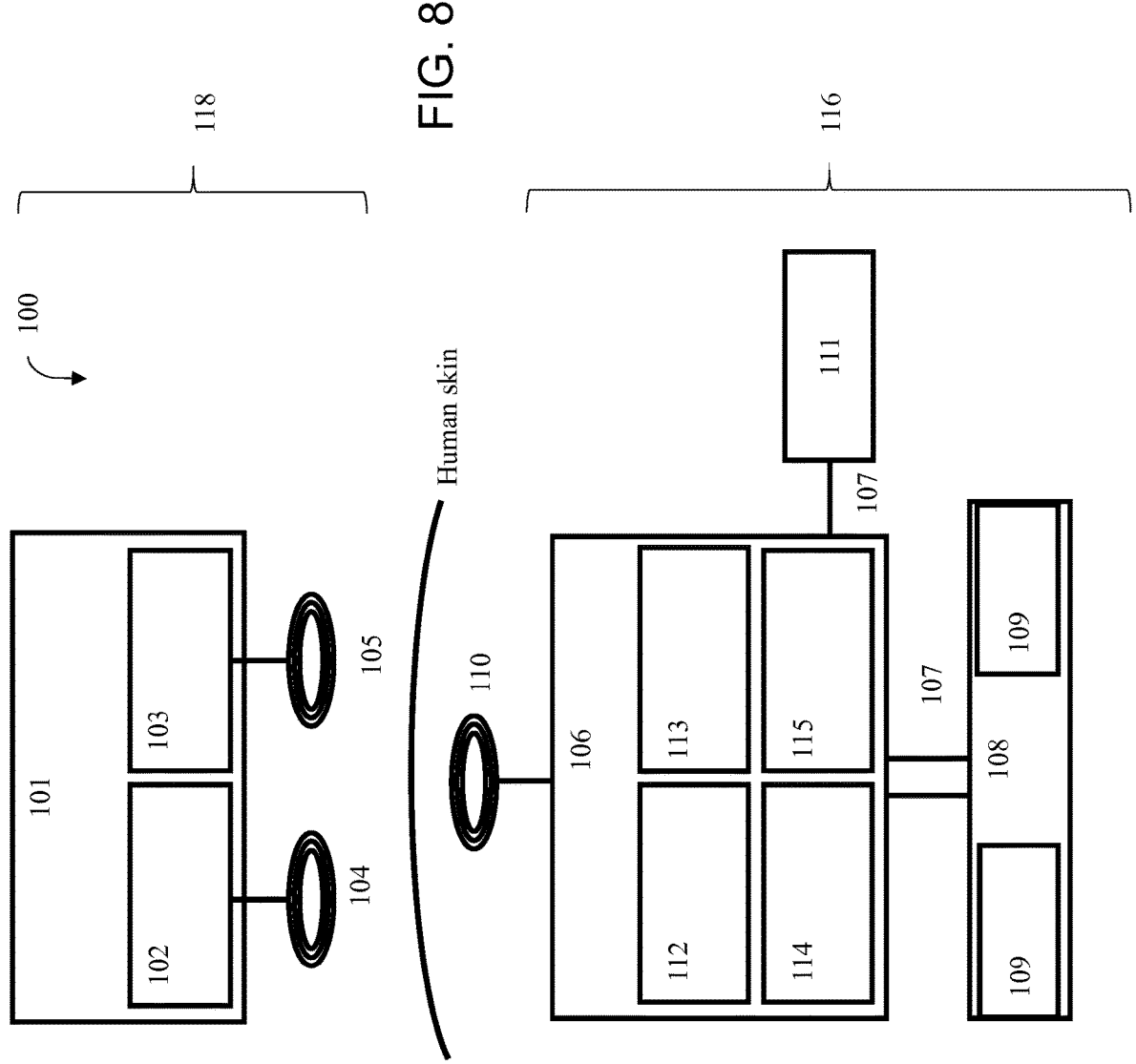

TREATMENT OF TYPE 1 DIABETES

This application is filed pursuant to 35 U.S.C. § 371 as a United States National Phase Application of International Patent Application Serial No. PCT/EP2018/061563 filed 4 May 2018, which claims priority to GB Application No. 1707207.5 filed 5 May 2017, and the entire contents of each of the foregoing applications are hereby incorporated by reference.

TECHNICAL FIELD

This invention relates to the treatment and prevention of type 1 diabetes, more particularly to methods and medical devices that deliver electromodulation therapy for such purposes.

BACKGROUND ART

Type 1 diabetes (T1D), also known as insulin-dependent diabetes mellitus or diabetes mellitus type 1, is an autoimmune disease that results from the destruction of insulin-producing pancreatic β cells by autoreactive immune cells [1].

Conventional treatments, such as insulin replacement therapy, fail to prevent long-term complications in subjects with T1D [2]. Chronic insulin replacement therapy is still associated with major side effects including potential for acute hypoglycaemia, chronic microvascular disease (retinopathy, nephropathy and neuropathy) and chronic macrovascular disease (heart disease and stroke).

The invention therefore aims to provide further and improved treatments and prevention of T1D.

SUMMARY OF THE INVENTION

The inventors found that modulation of the neural activity of a pancreas-related sympathetic nerve supplying the lymphatic system is capable of improving glycaemia control in diabetic Non-Obese Diabetic (NOD) mice. In particular, the stimulation of neural activity results in inhibition of T cell activation or migration to the pancreas. The results therefore suggest that applying a signal (e.g. an electrical signal) to a pancreas-related sympathetic nerve (e.g. a pancreas-related sympathetic nerve supplying the lymphatic system) to stimulate the neural activity of the nerve could be an effective strategy for treating or preventing type 1 diabetes (T1D).

Thus, the invention provides a method of treating or preventing T1D in a subject by reversibly modulating the neural activity of a pancreas-related sympathetic nerve. A preferred way of reversibly modulating (e.g. stimulating) the neural activity of the pancreas-related sympathetic nerve neural activity uses a device or system which applies a signal (e.g. an electrical signal) to the pancreas-related sympathetic nerve.

The invention also provides a method of treating or preventing T1D in a subject, comprising applying a signal to a pancreas-related sympathetic nerve in the subject to reversibly modulate (e.g. stimulate) the neural activity of the pancreas-related sympathetic nerve.

The invention provides an implantable device or system comprising at least one neural interfacing element, such as a transducer, preferably an electrode, suitable for placement on or around a pancreas-related sympathetic nerve, and a signal generator for generating a signal to be applied to the pancreas-related sympathetic nerve via the at least one neural interfacing element such that the signal reversibly modulates (e.g. stimulates) the neural activity of the pancreas-related sympathetic nerve to produce an improvement in one or more physiological parameters in the subject. The improvement in the physiological parameters may be one or more of the group consisting of: an increase in blood insulin level, a reduction in (fasting) blood glucose level, a reduction in glycated haemoglobin (HbA1c) level, a reduction in inflammation systemically (e.g. indicated by the levels of circulating cytokines, and/or C-reactive protein) or locally in the pancreas, such as insulitis (e.g. indicated by the levels of C-peptide, autoreactive T cells, and/or autoantibodies), and an increase in catecholamine levels in the pancreas. In certain embodiments, the improvement in the physiological parameters may be one or more of the group consisting of: an increase in GABA levels in the pancreas, and an increase in the number of pancreatic β cells in the pancreas.

The invention also provides a method of treating or preventing T1D in a subject, comprising: (i) implanting in the subject a device or system of the invention; (ii) positioning a neural interfacing element of the device or system in signaling contact with a pancreas-related sympathetic nerve in the subject; and optionally (iii) activating the device or system.

Similarly, as illustrated in FIG. 11, the invention provides a method 200 of reversibly modulating (e.g. stimulating) neural activity in a pancreas-related sympathetic nerve in a subject, comprising: (i) 210 implanting in the subject a device or system of the invention; (ii) 220 positioning a neural interfacing element in signaling contact with a pancreas-related sympathetic nerve in the subject; and optionally (iii) 230 activating the device or system.

The invention also provides a method of implanting a device or a system of the invention in a subject, comprising: positioning a neural interfacing element of the device or system in signaling contact with a pancreas-related sympathetic nerve in the subject.

Optionally, the methods of the invention may comprise administering GABA, a GABA analogue, or a GABA-enhancing agent to the subject. For example, GABA, a GABA analogue, or a GABA-enhancing agent may be administered before, during or after activation of the device or system of the invention implanted and positioned in the subject. The GABA-enhancing agent may be selected from the group consisting of benzodiazepines such as diazepam, alprazolam, clonazepam, lorazepam, or chloradiazepozide; barbituates such as phenobarbital, pentobarbital, butobarbital, amobarbital, secobarbital or thiopental; baclofen; acamprosate; pregabalin; gabapentin; tiagabine; lamotrigine; topiramate; neuroactive steroids such as allopregnalone or ganaxolone; nabiximols such as sativex; and combinations thereof.

The invention also provides a device or a system of the invention, wherein the device or system is attached to a pancreas-related sympathetic nerve.

The invention also provides the use of a device or system for treating or preventing T1D in a subject, by reversibly modulating (e.g. stimulating) the neural activity in a pancreas-related sympathetic nerve in the subject.

The invention also provides a charged particle for use in a method of treating or preventing T1D, wherein the charged particle causes reversible depolarization of the nerve membrane of a pancreas-related sympathetic nerve, such that an action potential is generated de novo in the modified nerve.

The invention also provides a modified pancreas-related sympathetic nerve to which a neural interfacing element of the system or device of the invention is attached. The neural interfacing element is in signaling contact with the pancreas-related sympathetic nerve and so the pancreas-related sympathetic nerve can be distinguished from the pancreas-related sympathetic nerve in its natural state. Furthermore, the nerve is located in a subject who suffers from or is at risk of developing T1D.

The invention also provides a modified pancreas-related sympathetic nerve, wherein the neural activity is reversibly modulated (e.g. stimulated) by applying a signal to the pancreas-related sympathetic nerve.

The invention also provides a modified pancreas-related sympathetic nerve, wherein the nerve membrane is reversibly depolarized by an electric field, such that an action potential is generated de novo in the modified pancreas-related sympathetic nerve.

The invention also provides a modified pancreas-related sympathetic nerve bounded by a nerve membrane, comprising a distribution of potassium and sodium ions movable across the nerve membrane to alter the electrical membrane potential of the nerve so as to propagate an action potential along the nerve in a normal state; wherein at least a portion of the pancreas-related sympathetic nerve is subject to the application of a temporary external electrical field which modifies the concentration of potassium and sodium ions within the nerve, causing depolarization of the nerve membrane, thereby, in a disrupted state, temporarily generating an action potential de novo across that portion; wherein the nerve returns to its normal state once the external electrical field is removed.

The invention also provides a modified pancreas-related sympathetic nerve obtainable by reversibly modulating (e.g. stimulating) neural activity of the pancreas-related sympathetic nerve according to a method of the invention.

The invention also provides a method of modifying a pancreas-related sympathetic nerve's activity, comprising a step of applying a signal to the pancreas-related sympathetic nerve in order to reversibly modulate (e.g. stimulate) the neural activity of the pancreas-related sympathetic nerve in a subject.

Preferably the method does not involve a method for treatment of the human or animal body by surgery. The subject already carries a device or system of the invention which is in signaling contact with the pancreas-related sympathetic nerve.

The invention also provides a method of controlling a device or system of the invention which is in signaling contact with the pancreas-related sympathetic nerve, comprising a step of sending control instructions to the device or system, in response to which the device or system applies a signal to the pancreas-related sympathetic nerve.

DETAILED DESCRIPTION OF THE INVENTION

A Pancreas-Related Sympathetic Nerve

The pancreas is innervated by nerves of the autonomous system including the sympathetic nervous system, which contributes to the body's glycaemic control [3]. The sympathetic splanchnic nerve, arising from the paraspinal sympathetic trunks, is the primary sympathetic influence on the pancreas.

The invention involves modulating a pancreas-related sympathetic nerve, preferably a pancreas-related sympathetic nerve supplying the lymphatic system of the pancreas. The lymphatic system of the pancreas is a complex, intricate network of lymphatic vessels and nodes that follow the course of the arteries and arterioles (for review, see [4]).

The inventors confirmed that the lymphatic system of the pancreas is innervated by sympathetic catecholaminergic fibers. Interestingly, the inventors found that modulation (e.g. stimulation) of a pancreas-related sympathetic nerve supplying the lymphatic system of the pancreas is capable of improving glycaemic control by inhibiting T cell activation or migration to the pancreas. Previous studies in animal models have shown that autoreactive T cells play a critical role in type 1 diabetes (T1D) initiation and progression, and that their activation occurs in the lymphatic system of the pancreas. Hence, modulation (e.g. stimulation) of the neural activity of a pancreas-related sympathetic nerve may be useful for treating or preventing T1D.

The invention involves modulating neural activity at any site along a pancreas-related sympathetic nerve, preferably a pancreas-related sympathetic nerve supplying the lymphatic system of the pancreas. For example, the site may be at the surface of the pancreas, e.g. at the head, neck, body or tail of the pancreas, or the site along a pancreas-related sympathetic nerve may be at one or more branches of the splenic arterial bundle, for example where it innervates the pancreatic parenchyma. The site may be adjacent to a blood vessel in the pancreas, e.g. the gastroduodenal artery, the pancreaticoduodenal artery, the splenic artery, the pancreatic artery, or branches thereof. Preferably, the site is at the head of the pancreas, e.g. adjacent to an artery, such as the gastroduodenal artery, or the pancreaticoduodenal artery. Preferably, the site is amenable for the attachment of electrodes.

The nerve to be modulated may contain fibers that only supply the lymphatic system of the pancreas. In these embodiments, the invention may involve applying a signal to modulate all the fibers within the nerve.

Alternatively, the nerve to be modulated may contain a mixture of fibers supplying the lymphatic system and other parts of the pancreas (e.g. islet cells). In these embodiments, the invention may involve selective modulation of the nerve by applying a signal to modulate only a portion of the nerve, such that only some of the fibers (e.g. fibers supplying the lymphatic system of the pancreas) within the nerve are modulated. Thus, the invention may additionally involve a step of identifying a pancreas-related sympathetic nerve supplying the lymphatic system of the pancreas (and/or fibers thereof) prior to applying a signal. Methods of selective modulation of nerve fibers within a nerve are known in the art (e.g. see [5], [6] and [7]).

Where the invention refers to a modified pancreas-related sympathetic nerve (e.g. a modified pancreas-related sympathetic nerve supplying the lymphatic system of the pancreas), this nerve is ideally present in situ in a subject.

Modulation of Neural Activity

According to the invention, applying a signal (e.g. an electrical signal) to a pancreas-related sympathetic nerve results in neural activity in at least part of the nerve being modulated. Modulation of neural activity, as used herein, is taken to mean that the signaling activity of the nerve is altered from the baseline neural activity—that is, the signaling activity of the nerve in the subject prior to any intervention. Such modulation may stimulate or otherwise change the neural activity compared to baseline activity. As used herein, "neural activity" of a nerve means the signaling activity of the nerve, for example the amplitude, frequency and/or pattern of action potentials in the nerve. The term "pattern", as used herein in the context of action potentials in the nerve, is intended to include one or more of: local field potential(s), compound action potential(s), aggregate action potential(s), and also magnitudes, frequencies, areas under the curve and other patterns of action potentials in the nerve or sub-groups (e.g. fascicules) of neurons therein.

One advantage of the invention is that modulation of neural activity is reversible. Hence, the modulation of neural activity is not permanent. For example, upon cessation of the application of a signal, neural activity in the nerve returns substantially towards baseline neural activity within 1-60 seconds, or within 1-60 minutes, or within 1-24 hours (e.g. within 1-12 hours, 1-6 hours, 1-4 hours, 1-2 hours), or within 1-7 days (e.g. 1-4 days, 1-2 days). In some instances of reversible modulation, the neural activity returns substantially fully to baseline neural activity. That is, the neural activity following cessation of the application of a signal is substantially the same as the neural activity prior to a signal being applied. Hence, the nerve or the portion of the nerve has regained its normal physiological capacity to propagate action potentials.

In other embodiments, modulation of neural activity may be substantially persistent. As used herein, "persistent" is taken to mean that the modulated neural activity has a prolonged effect. For example, upon cessation of the application of a signal, neural activity in the nerve remains substantially the same as when the signal was being applied—i.e. neural activity during and following signal application is substantially the same. Reversible modulation is preferred.

Stimulation of the neural activity may be partial stimulation. Partial stimulation may be such that the total signaling activity of the whole nerve is partially increased, or that the total signaling activity of a subset of nerve fibers of the nerve is fully increased (i.e. there is no neural activity in that subset of fibers of the nerve), or that the total signaling of a subset of nerve fibers of the nerve is partially increased compared to baseline neural activity in that subset of fibers of the nerve.

According to the invention, stimulation refers to neural activity in at least part of a pancreas-related sympathetic nerve being increased compared to baseline neural activity in that part of the nerve. This increase in activity can be across the whole nerve, in which case neural activity is increased across the whole nerve.

The invention typically involves stimulation of neural activity. Stimulation of neural activity, as used herein, is taken to mean that the signaling activity of the nerve is increased from the baseline neural activity—that is, the signaling activity of the nerve in the subject prior to any intervention. For example, stimulation typically involves increasing neural activity e.g. generating action potentials beyond the point of the stimulation in at least a part of the pancreas-related sympathetic nerve. At any point along the axon, a functioning nerve will have a distribution of potassium and sodium ions across the nerve membrane. The distribution at one point along the axon determines the electrical membrane potential of the axon at that point, which in turn influences the distribution of potassium and sodium ions at an adjacent point, which in turn determines the electrical membrane potential of the axon at that point, and so on. This is a nerve operating in its normal state, wherein action potentials propagate from point to adjacent point along the axon, and which can be observed using conventional experimentation.

One way of characterizing a stimulation of neural activity is a distribution of potassium and sodium ions at one or more points in the axon, which is created not by virtue of the electrical membrane potential at adjacent a point or points of the nerve as a result of a propagating action potential, but by virtue of the application of a temporary external electrical field. The temporary external electrical field artificially modifies the distribution of potassium and sodium ions within a point in the nerve, causing depolarization of the nerve membrane that would not otherwise occur. The depolarization of the nerve membrane caused by the temporary external electrical field generates de novo action potential across that point. This is a nerve operating in a disrupted state, which can be observed by a distribution of potassium and sodium ions at a point in the axon (the point which has been stimulated) that has an electrical membrane potential that is not influenced or determined by a the electrical membrane potential of an adjacent point.

Stimulation of neural activity is thus understood to be increasing neural activity from continuing past the point of signal application. Thus, the nerve at the point of signal application is modified in that the nerve membrane is reversibly depolarized by an electric field, such that a de novo action potential is generated and propagates through the modified nerve. Hence, the nerve at the point of signal application is modified in that a de novo action potential is generated.

When an electrical signal is used with the invention, the stimulation is based on the influence of electrical currents (e.g. charged particles, which may be one or more electrons in an electrode attached to the nerve, or one or more ions outside the nerve or within the nerve, for instance) on the distribution of ions across the nerve membrane.

Stimulation of neural activity may be partial stimulation. Partial stimulation may be such that the total signaling activity of the whole nerve is partially increased, or that the total signaling activity of a subset of nerve fibers of the nerve is fully increased, or that the total signaling of a subset of nerve fibers of the nerve is partially increased compared to baseline neural activity in that subset of fibers of the nerve. For example, an increase in neural activity of 5%, 10%, 15%, 20%, 25%, 30%, 35%, 40%, 45%, 50%, 60%, 70%, 80%, 90% or 95%, or an increase of neural activity in a subset of nerve fibers of the nerve. The neural activity may be measured by methods known in the art, for example, by the number of action potentials which propagate through the axon and/or the amplitude of the local field potential reflecting the summed activity of the action potentials.

The invention may selectively stimulate nerve fibers of various sizes within a nerve. Larger nerve fibers tend to have a lower threshold for stimulation than smaller nerve fibers. Thus, for example, increasing signal amplitude (e.g. increasing amplitude of an electric signal) may generate stimulation of the smaller fibers as well as larger fibers. For example, asymmetrical (triangular instead of square pulse) waveforms may be used stimulate C-fiber (unmyelinated).

Modulation of neural activity may be an alteration in the pattern of action potentials. It will be appreciated that the pattern of action potentials can be modulated without necessarily changing the overall frequency or amplitude. For example, modulation of the neural activity may be such that the pattern of action potentials is altered to more closely resemble a healthy state rather than a disease state.

Modulation of neural activity may comprise altering neural activity in various other ways, for example increasing or decreasing a particular part of the neural activity and/or stimulating new elements of activity. Altering the neural activity may be in particular intervals of time, in particular frequency bands, according to particular patterns and so forth.

Modulation of neural activity may be (at least partially) corrective. As used herein, "corrective" is taken to mean that the modulated neural activity alters neural activity of a subject towards the pattern of neural activity in a healthy subject, and this is called axonal modulation therapy. That is, upon cessation of signal application, neural activity in the nerve more closely resembles (ideally, substantially fully resembles) the pattern of action potentials in the nerve observed in a healthy subject than prior to signal application. Such corrective modulation can be any modulation as defined herein. For example, application of a signal may result in a block on neural activity, and upon cessation of signal application the pattern of action potentials in the nerve resembles the pattern of action potentials observed in a healthy subject. By way of further example, application of the signal may result in neural activity resembling the pattern of action potentials observed in a healthy subject and, upon cessation of the signal, the pattern of action potentials in the nerve remains the pattern of action potentials observed in a healthy subject.

Type 1 Diabetes

The invention provides a therapy for type 1 diabetes (T1D). The invention is useful for treating T1D, for example, suppressing, ameliorating or reversing the symptoms associated with T1D. The invention may also be useful for preventing T1D, for example, delaying the onset of or reducing the risk of developing the symptoms associated with T1D.

T1D is an autoimmune condition which results in the destruction of the pancreatic β cells leading to insulin deficiency and consequently hyperglycaemia. Typically, pancreatic β cells are progressively reduced over time ultimately resulting in the clinical onset of diabetes. β cell injury occurs due to the production of humoral autoantibodies against pancreatic cell components. During this period, additional injury occurs due to the onset of cellular T-cell autoimmunity (also for pancreatic cell components). The auto-reactive T cells first surround the islets and eventually invade the interior of the islets resulting in the progressive loss of functioning β cells. A progressive decrease in insulin production accompanies β cell destruction. At this stage, diagnosis of the diabetic condition is made using conventional tests, such as IVGTT (intravenous glucose tolerance test) and OGTT (oral glucose tolerance test). Subjects experiencing a loss of the first phase insulin response are often labeled "pre-diabetic" or impaired glucose tolerance (IGT); however symptoms heralding the clinical onset of diabetes frequently occur shortly after this diagnosis. The invention may be beneficial for subjects diagnosed as pre-diabetic or IGT, as well as those with established T1D.

Diagnostic criteria for pre-diabetes or IGT include: fasting plasma glucose level of between 110 to 125 mg/dL (6.1 mmol/L to 6.9 mmol/L). Alternatively, the subject may show a plasma glucose level of between 140 to 199 mg/dL (7.8 mmol/L to 11.0 mmol/L) at two times points during a glucose tolerance test (GTT), one of which must be within 2 hrs of ingestion of glucose. Alternatively, the glycated haemoglobin is between 5.7% and 6.4%.

Diagnostic criteria that establish a subject as suffering from T1D include fasting plasma glucose levels in excess of 126 mg/dL (7 mmol/L), e.g. between about 140 to about 200 mg/dl. (Normal plasma glucose levels are typically less than 100 mg/dl (<5.6 mmol/L).) Alternatively, subjects may show a plasma glucose level in excess of 200 mg/dL (11 mmol/L) at two times points during a glucose tolerance test (GTT), one of which must be within 2 hrs of ingestion of glucose.

A subject suitable for the invention may be any age, but will usually be ≤60, ≤50, ≤40, ≤30, ≤20, or ≤10 years old.

The invention is also useful for subjects who are at risk of developing T1D. Risk factors of T1D are known in the art. For example, the subject may have a family history of T1D, particularly from the mother. The subject may be genetically predisposed, e.g. if the subject carries certain variants of the HLA-DQA1, HLA-DQB1, and HLA-DRB1 genes. The subject may suffer from polyglandular autoimmune syndrome. The subject may also be suffering from thyroid diseases, a poorly working adrenal gland, and/or other immune system disorders. The subject may have a high level of glutamic acid decarboxylase autoantibodies e.g. serum GAD65 autoantibodies at ≥0.03 nmol/L.

Treatment of the T1D can be assessed in various ways, but typically involves an improvement in one or more physiological parameters of the subject. As used herein, an "improvement in a physiological parameter" is taken to mean that, for any given physiological parameter, an improvement is a change in the value of that parameter in the subject towards the normal value or normal range for that value—i.e. towards the expected value in a healthy subject.

As used herein, "worsening" of a physiological parameter is taken to mean that, for any given physiological parameter, worsening is a change in the value of that parameter in the subject away from the normal value or normal range for that value—i.e. away from the expected value in a healthy subject.

For example, in a subject having T1D, an improvement in a parameter may (depending on which abnormal values a subject is exhibiting) be any one of the group consisting of: an increase in blood insulin level, a reduction in (fasting) blood (e.g. plasma or serum) or urinary glucose level, a reduction in glycated haemoglobin (HbA1c) level, a reduction in inflammation systemically (e.g. indicated by the levels of circulating cytokines and/or C-reactive protein) or locally in the pancreas, such as insulitis (e.g. indicated by the levels of C-peptide, autoreactive T cells, and/or autoantibodies), and an increase in catecholamine levels in the pancreas. In certain embodiments, an improvement in a parameter may be any one of the group consisting of: an increase in GABA levels in the pancreas, and an increase in the number of pancreatic β cells in the pancreas. The invention might not lead to a change in all of these parameters. Suitable methods for determining the value for any given parameter will be appreciated by the skilled person.

Examples of autoreactive T cells are CD4+ T cells and CD8+ T cells.

Examples of autoantibodies include: islet cell cytoplasmic autoantibodies (ICA), insulin autoantibodies (IAA), glutamic acid decarboxylase autoantibodies (GADA), GAD65 autoantibodies, insulinoma-associated-2 autoantibodies (IA-2A), ICA512 autoantibodies, and protein tyrosine phosphatase-like autoantibodies.

As used herein, a physiological parameter is not affected by modulation of the neural activity of the pancreas-related sympathetic nerve if the parameter does not change (in response to the pancreas-related sympathetic nerve activity modulation) from the normal value or normal range for that value of that parameter exhibited by the subject or subject when no intervention has been performed i.e. it does not depart from the baseline value for that parameter.

Preferably, modulation of the neural activity of the pancreas-related sympathetic nerve has minimal impact on pancreatic blood flow. More preferably, modulation of the neural activity of the pancreas-related sympathetic nerve does not produce a change in pancreatic blood flow. Detecting any changes in pancreatic blood flow may thus be a useful physiological parameter for optimizing the parameters of the system or device of the invention. Pancreatic blood flow may be detected by invasive methods (e.g.

catheter-based blood flow measurements in the pancreatic artery) or non-invasive methods (e.g. ultrasound imaging).

The skilled person will appreciate that the baseline for any neural activity or physiological parameter in a subject need not be a fixed or specific value, but rather can fluctuate within a normal range or may be an average value with associated error and confidence intervals. Suitable methods for determining baseline values are well known to the skilled person. For example, a typical fasting plasma glucose level in a healthy human subject is less than 100 mg/dl (<5.6 mmol/L). By way of a further example, a typical HbA1c content in a healthy human subject is between 20-42 mmol/mol (4-5.6% of total Hb).

As used herein, a physiological parameter is detected in a subject when the value for that parameter exhibited by the subject at the time of detection is determined. A detector (e.g. a physiological sensor subsystem, a physiological data processing module, a physiological sensor, etc.) is any element able to make such a determination.

Thus, in certain embodiments, the invention further comprises a step of determining one or more physiological parameters of the subject, wherein the signal applied to the pancreas-related sympathetic nerve is applied only when the determined physiological parameter meets or exceeds a predefined threshold value. In such embodiments, wherein more than one physiological parameter is determined, the signal may be applied when any one of the determined parameters meets or exceeds its threshold value, alternatively only when all of the determined parameters meet or exceed their threshold values. In certain embodiments, wherein the signal is applied to the pancreas-related sympathetic nerve by a device/system of the invention, the device/system further comprises at least one detector configured to determine the one or more physiological parameters.

In certain embodiments of the method, the one or more physiological parameters are one or more of the group consisting of: blood insulin level, (fasting) blood or urinary glucose level, glycated haemoglobin (HbA1c) level, the extent of immune response and/or inflammation systemically (e.g. indicated by the levels of circulating cytokines and/or C-reactive protein) or locally in the pancreas (e.g. indicated by the levels of C-peptide, autoreactive T cells, and/or autoantibodies), catecholamine levels in the pancreas, pancreatic blood pressure and pancreatic blood flow. In certain embodiments of the method, the one or more physiological parameters are one or more of the group consisting of: an increase in GABA levels in the pancreas, and an increase in the number of pancreatic β cells in the pancreas.

In certain embodiments, the physiological parameter is an action potential or pattern of action potentials in a nerve of the subject, wherein the action potential or pattern of action potentials is associated with T1D. In certain such embodiments, the nerve is a pancreas-related sympathetic nerve.

A "predefined threshold value" for a physiological parameter is the minimum (or maximum) value for that parameter that must be exhibited by a subject or subject before the specified intervention is applied. For any given parameter, the threshold value may be defined as a value indicative of a pathological state or a disease state (e.g. the blood glucose level greater than a threshold level, or greater than the blood glucose level in a healthy subject). The threshold value may be defined as a value indicative of the onset of a pathological state or a disease state. Thus, depending on the predefined threshold value, the invention can be used as a prevention or a treatment. Alternatively, the threshold value may be defined as a value indicative of a physiological state of the subject (that the subject is, for example, asleep, post-prandial, or exercising). Appropriate values for any given parameter would be simply determined by the skilled person (for example, with reference to medical standards of practice).

Such a threshold value for a given physiological parameter is exceeded if the value exhibited by the subject is beyond the threshold value—that is, the exhibited value is a greater departure from the normal or healthy value for that parameter than the predefined threshold value.

In certain embodiments of the method, the method does not affect the pancreatic blood flow, and the non-β cells physiological functions of the pancreas (e.g. secretion of glucagon, somatostatin, pancreatic polypeptide, and pancreatic juice).

Suitable methods for determining the value for any given parameter would be appreciated by the skilled person, and explained further below.

A subject useful with the invention may, in addition to having an implant, receive medicine for their condition. For instance, a subject having an implant according to the invention may receive a diabetes medicine, e.g. insulin (e.g. regular insulin (Humulin 70/30, Novolin 70/30, others), insulin isophane (Humulin N, Novolin N), insulin glulisine (Apidra), insulin lispro (Humalog) and insulin aspart (Novolog), long-acting insulins such as glargine (Lantus) and detemir (Levemir)), artificial pancreas or β cells, pramlintide (Symlin), high blood pressure medicines (e.g. angiotensin-converting enzyme (ACE) inhibitros or angiotensin II receptor blockers (ARBs)), aspirin, and/or cholesterol-lowering drugs (which will usually continue medication which was occurring before receiving the implant). Thus the invention provides the use of these medicines in combination with a device/system of the invention.

In certain embodiments, the physiological parameter that is improved may be an increase in pancreatic β cells in the pancreas. The inventors have found that applying a signal of the invention to a pancreas-related sympathetic nerve supplying the lymphatic system of the pancreas may be used to increase the number of pancreatic β cells in the pancreas (see, for example, FIG. 9D). Increasing the number of pancreatic β cells may reduce hyperglycaemia associated with T1D. The signal of the invention may increase the number of pancreatic β cells by increasing the level of GABA in the pancreas. In certain embodiments, the invention may increase the secretion of GABA in the pancreas. In certain embodiments, the invention may increase the expression of GABA in the pancreas.

Without wishing to be bound by theory, it is noted that GABA has been shown to increase the mass of pancreatic β cells in pancreatic islets. GABA is thought to participate in maintaining β-cell mass and protect β-cells from apoptosis. GABA has also been shown to promote the conversion of α to β pancreatic cells in pancreatic islets [8]. The α- to β-conversion of pancreatic cells has also been shown to reactivate pancreatic cell neogenesis to replenish the mass of α pancreatic cells [9]. Therefore, long-term exposure to GABA is thought to promote pancreatic β cell hyperplasia, thereby providing a method for the treatment or prevention of T1D. In certain embodiments, the invention may be used to improve the level of secretion of GABA in the pancreas in a subject with T1D.

In certain embodiments, the invention may be used to increase the level of active GABA in the pancreas. As used herein, "GABA" refers to gamma-aminobutyric acid (the IUPAC of which is 4-aminobutanoic acid). "Active GABA" refers to bioavailable GABA that increases the number of pancreatic β cells in the pancreas. A "GABA analogue" refers to a compound which is an analogue or derivative of GABA, including a GABA prodrug. A "GABA-enhancing agent" refers to an agent that enhances or increases active GABA in the pancreas, including an increase in GABA activity or bioavailability. Examples of GABA-enhancing agents include (but are not necessarily limited to) benzodiazepines (e.g. diazepam, alprazolam, clonazepam, lorazepam, or chloradiazepozide), barbituates (e.g. phenobarbital, pentobarbital, butobarbital, amobarbital, secobarbital or thiopental) baclofen, acamprosate, pregabalin, gabapentin, tiagabine, lamotrigine, topiramate, neuroactive steroids (e.g. allopregnalone and ganaxolone), nabiximols (e.g. sativex), and combinations thereof.

In certain embodiments, a subject useful with the invention may, in addition to having an implant, receive a medicine or therapy that increases active GABA in the pancreas. For example, the subject may be receiving benzodiazepines (e.g. diazepam, alprazolam, clonazepam, lorazepam, or chloradiazepozide), barbituates (e.g. phenobarbital, pentobarbital, butobarbital, amobarbital, secobarbital or thiopental) baclofen, acamprosate, pregabalin, gabapentin, tiagabine, lamotrigine, topiramate, neuroactive steroids (e.g. allopregnalone and ganaxolone), nabiximols (e.g. sativex), electroconvulsive therapy or transcranial magnetic stimulation.

In certain embodiments, the invention may include a substance that increases active GABA in the pancreas, such as those medicines or therapies disclosed in the preceding paragraph, for use in a method of treating or preventing T1D in a subject receiving, having received, or about to receive, a method of reversibly modulating neural activity in a pancreas-related sympathetic nerve, comprising: (i) implanting in the subject a device or system of the invention; (ii) positioning the neural interfacing element in signaling contact with the pancreas-related sympathetic nerve; and optionally (iii) activating the device or system. Furthermore, the invention may include a substance that increases active GABA in the pancreas, such as those medicines or therapies disclosed in the preceding paragraph, for use in combination with a charged particle, such as one or more electrons, in a method of treating or preventing T1D, wherein the charged particle causes reversible depolarization of the nerve membrane of a pancreas-related sympathetic nerve, such that an action potential is generated de novo in the modified nerve.

An Implantable Device/System for Implementing the Invention

An implantable system for modulating neural activity according to the invention comprises an implantable device (e.g. implantable device 106 of FIG. 8). The implantable device comprises at least one neural interfacing element such as a transducer, preferably an electrode (e.g. electrode 108), suitable for placement on or around a pancreas-related sympathetic nerve. The implantable system preferably also comprises a processor (e.g. microprocessor 113) coupled to the at least one neural interfacing element.

The at least one neural interfacing element may take many forms, and includes any component which, when used in an implantable device or system for implementing the invention, is capable of applying a stimulus or other signal that modulates electrical activity in a nerve.

The various components of the implantable system are preferably part of a single physical device, either sharing a common housing or being a physically separated collection of interconnected components connected by electrical leads (e.g. leads 107). As an alternative, however, the invention may use a system in which the components are physically separate, and communicate wirelessly. Thus, for instance, the at least one neural interfacing element (e.g. electrode 108) and the implantable device (e.g. implantable device 106) can be part of a unitary device, or together may form an implantable system (e.g. implantable system 116). In both cases, further components may also be present to form a larger device or system (e.g. system 100).

Suitable Forms of a Modulating Signal

The invention uses signals which are applied via one or more neural interfacing elements (e.g. electrode 108) placed in signaling contact with a pancreas-related sympathetic nerve.

Signals applied according to the invention are ideally non-destructive. As used herein, a "non-destructive signal" is a signal that, when applied, does not irreversibly damage the underlying neural signal conduction ability of the nerve. That is, application of a non-destructive signal maintains the ability of the nerve (e.g. a pancreas-related sympathetic nerve) or fibers thereof, or other nerve tissue to which the signal is applied, to conduct action potentials when application of the signal ceases, even if that conduction is in practice artificially stimulated as a result of application of the non-destructive signal.

The signal will usually be an electrical signal, which may be, for example, a voltage or current waveform. As used herein, "charge-balanced" in relation to a DC current is taken to mean that the positive or negative charge introduced into any system (e.g. a nerve) as a result of a DC current being applied is balanced by the introduction of the opposite charge in order to achieve overall (net) neutrality. The at least one neural interfacing element (e.g. electrode 108) of the implantable system (e.g. implantable system 116) is configured to apply the electrical signals to a nerve, or a part thereof. However, electrical signals are just one way of implementing the invention, as is further discussed below.

An electrical signal can take various forms, for example, a voltage or current. In certain such embodiments the signal applied comprises a direct current (DC), such as a charge balanced direct current, or an alternating current (AC) waveform, or both a DC and an AC waveform. A combination of charge balanced DC and AC is particularly useful, with DC being applied for a short initial period after which only AC is used [10].

In certain embodiments, the DC waveform or AC waveform may be a square, sinusoidal, triangular, trapezoidal, quasitrapezodial or complex waveform. The DC waveform may alternatively be a constant amplitude waveform. In certain embodiments the electrical signal is an AC sinusoidal waveform. In other embodiments, waveform comprise one or more pulse trains, each comprising a plurality of charged-balanced biphasic pulses.

In any case, the signal may be applied in bursts. The range of burst durations may be from seconds to hours; applied continuously in a duty cycled manner from 0.01% to 100%, with a predetermined time interval between bursts. The electric signal may be applied as step change or as a ramp change in current or intensity. Particular signal parameters for modulating (e.g. stimulating) a pancreas-related sympathetic nerve are further described below.

Modulation or stimulation of the neural activity of the pancreas-related sympathetic nerve can be achieved using electrical signals which serve to replicate the normal neural activity of the nerve. Preferred embodiments of the electrical signals comprise a plurality of temporally separated pulse trains, each pulse train being made up of a plurality of pulses.

With reference again to FIG. 8, the implantable system 116 comprises an implantable device 106 which may comprise a signal generator 117 (not shown); for example, a pulse generator. When the implantable device comprises a pulse generator, the implantable device 106 may be referred to as an implantable pulse generator. The signal generator 117 may also be a voltage or current source. The signal generator 117 may be pre-programmed to deliver one or more pre-defined waveforms with parameters falling within the range given above. Alternatively, the signal generator 117 may be controllable to adjust one or more of the signal parameters described below. Control may be open loop, wherein the user or an operator of the implantable device 106 may configure the signal generator using an external controller (e.g. controller 101), or control may be closed loop, wherein signal generator modifies the signal parameters in response to one or more physiological parameters of the subject, as is further described below.

Signal Parameters for Modulating Neural Activity

In all of the above examples, the signal generator 117 may be configured to deliver an electrical signal for modulating (e.g. stimulating) a pancreas-related sympathetic nerve. In the invention, the signal generator 117 is configured to apply an electrical signal with certain signal parameters to modulate (e.g. stimulate) neural activity in a pancreas-related sympathetic nerve. Signal parameters for modulating (e.g. stimulating) the pancreas-related sympathetic nerve, which are described herein, may include waveform, amplitude, and frequency.

In embodiments where the nerve to be modulated contains a mixture of fibers supplying the lymphatic system and other parts of the pancreas (e.g. islet cells), signal parameters selectively modulate (e.g. stimulate) the neural activity of the fibers supplying the lymphatic system of the pancreas relative to the fibers supplying other parts of the pancreas. More particularly, the signal parameters may selectively modulate (e.g. stimulate) the neural activity of the fibers supplying the lymphatic system of the pancreas without modulating (e.g. stimulating) neural activity the fibers supplying other parts of the pancreas. Appropriate signal parameters for selective modulation may be frequency and/or amplitude, and the parameters may be optimized by, for example, identifying values that provide better on-target effects (e.g. decrease in blood glucose level) relative to off-target effects (e.g. pancreatic blood flow), or by minimizing off-target effects, e.g. no change in pancreatic blood flow.

In some embodiments, the electrical signal has a frequency of between 0.1 Hz to 100 Hz, preferably between 0.1 Hz and 50 Hz, more preferably between 1 Hz and 20 Hz. The frequency may advantageously be between 1 Hz and 10 Hz. Frequencies of 5 Hz, 10 Hz, 15 Hz and particularly 20 Hz are particularly preferred, though any frequency within the range may be chosen.

In some embodiments, the electrical signal has a current up to and including 10 mA, such as between 0.01 mA and 10 mA, or between 0.1 mA to 10 mA. Preferably, the electrical signal has a current of less than 5 mA, such as between 0.01 mA and 5 mA, or between 0.1 mA and 5 mA.

The signal generator 117 may be configured to deliver one or more pulse trains at intervals according to the above-mentioned frequencies. For example, a frequency of 10 to 100 Hz results in a pulse interval between 10 pulses per second and 100 pulses per second, within a given pulse train. Accordingly, the range of pulse widths may be from 0.01 to 2 ms (including both positive and negative phases of the pulse, in the case of a charged-balanced biphasic pulse). The range of pulse amplitudes may be from 0.01 to 10 mA peak-to-peak. For stimulating neural activity, advantages have been noted in respect of pulses of shorter pulse widths and lower amplitudes. In particular pulse widths between 0.2 ms and 0.5 ms and pulse amplitudes between 0.01 mA and 5 mA are preferred, though waveforms with pulse widths between 50 µs and 1 ms and pulse amplitudes between 0.20 mA and 0.65 mA are also advantageous.

Alternatively, modulating the pancreas-related sympathetic nerve with an electrode array may cause modulation (e.g. stimulate) the neural activity towards autoreactive T cells to a greater extent than towards the pancreatic β cells, as is described further below.

It will be appreciated by the skilled person that the current amplitude of an applied electrical signal necessary to achieve the intended modulation of the neural activity will depend upon the positioning of the electrode and the associated electrophysiological characteristics (e.g. impedance). It is within the ability of the skilled person to determine the appropriate current amplitude for achieving the intended modulation of the neural activity in a given subject.

Electrodes

As mentioned above, the implantable system comprises at least one neural interfacing element, the neural interfacing element is preferably an electrode 108. The neural interface is configured to at least partially and preferably fully circumvent the pancreas-related sympathetic nerve. The geometry of the neural interface is defined in part by the anatomy of the pancreas-related sympathetic nerve. In particular, the geometries may be limited by the length of the pancreas-related sympathetic nerve that is amenable for electrode attachment, and/or by the diameter of the pancreas-related sympathetic nerve, which may be about 0.5-10 µm (preferably about 1 µm).

In some embodiments (for example, FIG. 8), electrode 108 may be coupled to implantable device 106 of implantable system 116 via electrical leads 107. Alternatively, implantable device 106 may be directly integrated with the electrode 108 without leads. In any case, implantable device 106 may comprise DC current blocking output circuits, optionally based on capacitors and/or inductors, on all output channels (e.g. outputs to the electrode 108, or physiological sensor 111). Electrode 108 may be shaped as one of the group consisting of: a rectangle, an oval, an ellipsoid, a rod, a straight wire, a curved wire, a helically wound wire, a barb, a hook, or a cuff. In addition to electrode 108 which, in use, is located on, in, or near a pancreas-related sympathetic nerve, there may also be a larger indifferent electrode placed 119 (not shown) in the adjacent tissue.

Preferably, electrode 108 may contain at least two electrically conductive exposed contacts 109 configured, in use, to be placed on, in, or near a pancreas-related sympathetic nerve. Exposed contacts 109 may be positioned, in use, transversely along the axis of a pancreas-related sympathetic nerve. In this configuration, the distance between each of the at least two exposed contacts may be between about 0.5 mm and about 5 mm, optionally between about 1 mm and 3 mm, optionally between about 1 mm and 2 mm. Each of the at least two exposed contacts 109 may have a surface area in contact with a pancreas-related sympathetic nerve which is equal to that of the other. The surface area may range between about 0.1 mm$^2$ and about 100 mm$^2$, optionally between about 1 mm$^2$ to 50 mm$^2$, optionally between about 1 mm$^2$ to 20 mm$^2$, optionally about 5 mm$^2$ to 10 mm$^2$.

In some embodiments, electrode 108 for use in the present invention is an electrode array. Electrode arrays are capable of stimulating the nerve in a selective manner, as is known (see, e.g. [5], [6], [7]). Selective modulation of a pancreas-related sympathetic nerve is particularly useful for modulating (e.g. stimulating) selected nerve fibers, and thus for selectively modulating (e.g. stimulating) a pancreas-related sympathetic nerve fibers supplying the lymphatic system of the pancreas relative to other pancreas-related autonomic nerve fibers, if present.

The electrode arrays may be of the penetrating or non-penetrating type. A suitable electrode array may be an ICS-96 MultiPort planar array from Blackrock Microsystems. One possible configuration has 90 channels: 4×10 and 5×10 split planar arrays, with approximately 2,000 mm² surface area, 1 mm shaft length, and 0.4 mm interelectrode spacing.

Exposed contacts 109 may be insulated by a non-conductive biocompatible material, which may be spaced transversely along the pancreas-related sympathetic nerve in use.

Other Suitable Forms of Neural Interfacing Element and Signal

The signal may use thermal energy, and the temperature of a nerve can be modified to stimulate the propagation of neural activity. Heating the nerve can be used to modulate neural activity. In certain such embodiments, the neural interface is a small implantable or wearable transducer or device for radiant electromagnetic heating using visible, infrared, or microwave radiation, for example using a laser diode or a light emitting diode. In certain such embodiments, the radiant signal has an energy density less than 500 mW/cm². Further, in certain embodiments, the radiant signal is modulated with a modulation frequency of less than 5 Hz, optionally 1 Hz. In certain alternative embodiments, the neural interface is a small implantable or wearable transducer or device for conductive heating, such as an electrically resistive element, which can be used to provide a fast, reversible, and spatially very localized heating effect (see for example reference [11]). In certain embodiments, the signal increases the temperature of the nerve by up to 5° C.

The signal may comprise a mechanical signal. In certain embodiments, the mechanical signal is a pressure signal. In certain such embodiments, the neural interface is a transducer which generates pressure of up to 250 mmHg to be applied to the nerve which stimulates neural activity.

In certain alternative embodiments, the signal is an ultrasonic signal. In certain such embodiments, the neural interface is an ultrasound transducer, and the ultrasonic signal has a frequency below 0.5 MHz, optionally 0.1-0.5 MHz, optionally 0.1 MHz. In certain embodiments, the ultrasonic signal has a density of below 10 W/cm², for example 1.5 W/cm² or 9.5 W/cm².

Another mechanical form of signal for modulating neural activity uses ultrasound which may conveniently be implemented using external, for example wearable, instead of implanted, ultrasound transducers.

Microprocessor

The implantable system 116, in particular the implantable device 106, may comprise a processor, for example microprocessor 113. Microprocessor 113 may be responsible for triggering the beginning and/or end of the signals delivered to the nerve (e.g., a pancreas-related sympathetic nerve) by the at least one neural interfacing element. Optionally, microprocessor 113 may also be responsible for generating and/or controlling the parameters of the signal.

Microprocessor 113 may be configured to operate in an open-loop fashion, wherein a pre-defined signal (e.g. as described above) is delivered to the nerve at a given periodicity (or continuously) and for a given duration (or indefinitely) with or without an external trigger, and without any control or feedback mechanism. Alternatively, microprocessor 113 may be configured to operate in a closed-loop fashion, wherein a signal is applied based on a control or feedback mechanism. As described elsewhere herein, the external trigger may be an external controller 101 operable by the user or operator to initiate delivery of a signal.

Microprocessor 113 of the implantable system 116, in particular of the implantable device 106, may be constructed so as to generate, in use, a preconfigured and/or user-selectable signal that is independent of any input. Preferably, however, microprocessor 113 is responsive to an external signal, more preferably information (e.g. data) pertaining to one or more physiological parameters of the subject.

Microprocessor 113 may be triggered upon receipt of a signal generated by a user or an operator (e.g. a physician or by the subject in which the device 116 is implanted). To that end, the implantable system 116 may be part of a system which additionally comprises an external system 118 comprising a controller 101. An example of such a system is described below with reference to FIG. 8.

External system 118 of system 100 is external the implantable system 116 and external to the subject, and comprises controller 101. Controller 101 may be used for controlling and/or externally powering implantable system 116. To this end, controller 101 may comprise a powering unit 102 and/or a programming unit 103. The external system 118 may further comprise a power transmission antenna 104 and a data transmission antenna 105, as is further described below.

The controller 101 and/or microprocessor 113 may be configured to apply any one or more of the above signals to the nerve intermittently or continuously. Intermittent application of a signal involves applying the signal in an (on-off)$_n$ pattern, where n>1. For instance, the signal can be applied continuously for at least 5 days, optionally at least 7 days, before ceasing for a period (e.g. 1 day, 2 days, 3 days, 1 week, 2 weeks, 1 month), before being again applied continuously for at least 5 days, etc. Thus the signal is applied for a first time period, then stopped for a second time period, then reapplied for a third time period, then stopped for a fourth time period, etc. In such an embodiment, the first, second, third and fourth periods run sequentially and consecutively. The duration of the first, second, third and fourth time periods is independently selected. That is, the duration of each time period may be the same or different to any of the other time periods. In certain such embodiments, the duration of each of the first, second, third and fourth time periods may be any time from 1 second (s) to 10 days (d), 2 s to 7 d, 3 s to 4 d, 5 s to 24 hours (24 h), 30 s to 12 h, 1 min to 12 h, 5 min to 8 h, 5 min to 6 h, 10 min to 6 h, 10 min to 4 h, 30 min to 4 h, 1 h to 4 h. In certain embodiments, the duration of each of the first, second, third and fourth time periods is 5 s, 10 s, 30 s, 60 s, 2 min, 5 m, 10 min, 20 m, 30 min, 40 min, 50 m, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 2 d, 3 d, 4 d, 5 d, 6 d, 7 d.

In certain embodiments, the signal is applied by controller 101 and/or microprocessor for a specific amount of time per day. In certain such embodiments, the signal is applied for 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day. In certain such embodiments, the signal is applied continuously for the specified amount of time. In certain alternative such embodiments, the signal may be applied discontinuously across the day, provided the total time of application amounts to the specified time.

Continuous application may continue indefinitely, e.g. permanently. Alternatively, the continuous application may be for a minimum period, for example the signal may be continuously applied for at least 5 days, or at least 7 days.

Whether the signal applied to the nerve is controlled by controller 101, or whether the signal is continuously applied directly by microprocessor 113, although the signal might be a series of pulses, the gaps between those pulses do not mean the signal is not continuously applied.

In certain embodiments, the signal is applied only when the subject is in a specific state e.g. only when the subject is awake, only when the subject is asleep, prior to and/or after the ingestion of food, prior to and/or after the subject undertakes exercise, etc.

The various embodiments for timing for modulation of neural activity in the nerve can all be achieved using controller 101 in a device/system of the invention.

Other Components of the System Including the Implantable Device

In addition to the aforementioned electrode 108 and microprocessor 113, the implantable system 116 may comprise one or more of the following components: implantable transceiver 110; physiological sensor 111; power source 112; memory 114; and physiological data processing module 115. Additionally or alternatively, the physiological sensor 111; memory 114; and physiological data processing module 115 may be part of a sub-system external to the implantable system. Optionally, the external sub-system may be capable of communicating with the implantable system, for example wirelessly via the implantable transceiver 110.

In some embodiments, one or more of the following components may preferably be contained in the implantable device 106: power source 112; memory 114; and a physiological data processing module 115.

The power source 112 may comprise a current source and/or a voltage source for providing the power for the signal delivered to a pancreas-related sympathetic nerve by the electrode 108. The power source 112 may also provide power for the other components of the implantable device 106 and/or implantable system 116, such as the microprocessor 113, memory 114, and implantable transceiver 110. The power source 112 may comprise a battery, the battery may be rechargeable.

It will be appreciated that the availability of power is limited in implantable devices, and the invention has been devised with this constraint in mind. The implantable device 106 and/or implantable system 116 may be powered by inductive powering or a rechargeable power source.

Memory 114 may store power data and data pertaining to the one or more physiological parameters from internal system 116. For instance, memory 114 may store data pertaining to one or more signals indicative of the one or more physiological parameters detected by physiological sensor 111, and/or the one or more corresponding physiological parameters determined via physiological data processing module 115. In addition or alternatively, memory 114 may store power data and data pertaining to the one or more physiological parameters from external system 118 via the implantable transceiver 110. To this end, the implantable transceiver 110 may form part of a communication subsystem of the system 100, as is further discussed below.

Physiological data processing module 115 is configured to process one or more signals indicative of one or more physiological parameters detected by the physiological sensor 111, to determine the one or more corresponding physiological parameters. Physiological data processing module 115 may also be configured for reducing the size of the data pertaining to the one or more physiological parameters for storing in memory 114 and/or for transmitting to the external system via implantable transceiver 110. Implantable transceiver 110 may comprise one or more antenna(e). The implantable transceiver 100 may use any suitable signaling process such as RF, wireless, infrared and so on, for transmitting signals outside of the body, for instance to system 100 of which the implantable system 116 is one part.

Alternatively or additionally, physiological data processing module 115 may be configured to process the signals indicative of one or more physiological parameters and/or the determined one or more physiological parameters and determine the evolution of T1D in the subject. In such case, the implantable system 116, in particular the implantable device 106, will include a capability of calibrating and tuning the signal parameters for application to the pancreas-related sympathetic nerve based on the one or more physiological parameters and the determined evolution of T1D in the subject, as is further discussed below.

The physiological data processing module 115 and the at least one physiological sensor 111 may form a physiological sensor subsystem, either as part of the implantable system 116, part of the implantable device 106, or external to the implantable system.

Physiological sensor 111 comprises one or more sensors, each configured to detect a signal indicative of one of the one or more of the physiological parameters described above. For example, the physiological sensor 111 is configured for one or more of: detecting electrodermal activity using an electrical sensor for detecting electroretinographic activity using an electrical sensor; detecting biomolecule concentration using electrical, RF or optical (visible, infrared) biochemical sensors; detecting pancreatic blood flow using invasive methods (e.g. a catheter-based sensor in the pancreatic artery or non-invasive methods (e.g. ultrasound imaging); or a combination thereof.

The physiological parameters determined by the physiological data processing module 115 may be used to trigger the microprocessor 113 to deliver a signal of the kinds described above to a pancreas-related sympathetic nerve using the electrode 108. Upon receipt of signal indicative of a physiological parameter received from physiological sensor 111, the physiological data processor 115 may determine the physiological parameter of the subject, and the evolution of T1D in accordance, by calculating with techniques known in the art.

The memory 114 may store data pertaining to normal levels of one or more physiological parameters, i.e. the levels found in a healthy subject. The data may be specific to the subject into which the implantable system 116 is implanted, and gleaned from various tests known in the art. Upon receipt of a signal indicative of a physiological parameter received from physiological sensor 111, or else periodically or upon demand from physiological sensor 111, the physiological data processor 115 may determine and compare the physiological parameter detected by physiological sensor 111 with the data pertaining to a normal level of the physiological parameters stored in the memory 114 and determine whether the received signals are indicative of insufficient or excessive of a particular physiological parameter, and thus indicative of the evolution of T1D in the subject.

The implantable system 116 and/or implantable device 106 may be configured such that if and when an insufficient or excessive level of a physiological parameter is determined by the physiological data processor 115, the physiological data processor 115 triggers delivery of a signal to a pancreas-related sympathetic nerve by the electrode 108, in the manner described elsewhere herein. For instance, if a physiological parameter indicative of worsening of any of the physiological parameters and/or T1D, and/or of the onset of T1D, is determined, the physiological data processor 115 may trigger delivery of a signal which dampens secretion of the respective biochemical, as described elsewhere herein. Particular physiological parameters relevant to the present invention are described above. When one or more of these physiological parameters are determined by the physiological data processor 115, a signal may be applied to a pancreas-related sympathetic nerve via the electrode 108.

As an alternative to, or in addition to, the ability of the implantable system 116 and/or implantable device 106 to respond to physiological parameters, the microprocessor 113 may be triggered upon receipt of a signal generated by a user or an operator (e.g. a physician or by the subject in which the system 116 is implanted). To that end, the implantable system 116 may be part of a system 100 which comprises external system 118 and controller 101, as is further described below.

System Including Implantable Device

With reference to FIG. 8, the implantable device 106 of the invention may be part of a system 110 that includes a number of subsystems, for example the implantable system 116 and the external system 118. The external system 118 may be used for powering and programming the implantable system 116 and/or the implantable device 106 through human skin and underlying tissues.

The external subsystem 118 may comprise, in addition to controller 101, one or more of: a powering unit 102, for wirelessly recharging the battery of power source 112 used to power the implantable device 106; and, a programming unit 103 configured to communicate with the implantable transceiver 110. The programming unit 103 and the implantable transceiver 110 may form a communication subsystem. In some embodiments, powering unit 102 is housed together with programing unit 103. In other embodiments, they can be housed in separate devices.

The external subsystem 118 may also comprise one or more of: power transmission antenna 104; and data transmission antenna 105. Power transmission antenna 104 may be configured for transmitting an electromagnetic field at a low frequency (e.g., from 30 kHz to 10 MHz). Data transmission antenna 105 may be configured to transmit data for programming or reprogramming the implantable device 106, and may be used in addition to the power transmission antenna 104 for transmitting an electromagnetic field at a high frequency (e.g., from 1 MHz to 10 GHz). The temperature in the skin will not increase by more than 2 degrees Celsius above the surrounding tissue during the operation of the power transmission antenna 104. The at least one antennae of the implantable transceiver 110 may be configured to receive power from the external electromagnetic field generated by power transmission antenna 104, which may be used to charge the rechargeable battery of power source 112.

The power transmission antenna 104, data transmission antenna 105, and the at least one antennae of implantable transceiver 110 have certain characteristics such a resonant frequency and a quality factor (Q). One implementation of the antenna(e) is a coil of wire with or without a ferrite core forming an inductor with a defined inductance. This inductor may be coupled with a resonating capacitor and a resistive loss to form the resonant circuit. The frequency is set to match that of the electromagnetic field generated by the power transmission antenna 105. A second antenna of the at least one antennae of implantable transceiver 110 can be used in implantable system 116 for data reception and transmission from/to the external system 118. If more than one antenna is used in the implantable system 116, these antennae are rotated 30 degrees from one another to achieve a better degree of power transfer efficiency during slight misalignment with the with power transmission antenna 104.

External system 118 may comprise an external physiological sensor 121 (not shown) to detect signals indicative of one or more physiological parameters. The signals may be transmitted to the implantable system 116 via the at least one antennae of implantable transceiver 110. Alternatively or additionally, the signals may be transmitted to the external system 116 and then to the implantable system 116 via the at least one antennae of implantable transceiver 110. As with signals indicative of one or more physiological parameters detected by the implanted physiological sensor 111, the signals indicative of one or more physiological parameters detected by the external sensor 121 may be processed by the physiological data processing 115 to determine the one or more physiological parameters and/or stored in memory 114 to operate the implantable system 116 in a closed-loop fashion. The one or more physiological parameters determined from the external sensor 121 may be used in addition to alternatively to the one or more physiological parameters determined by the implanted physiological sensor 111.

In an embodiment according to the present application, the external physiological sensor 121 is a ultrasound imaging system which detects a signal indicative of blood flow.

The system 100 may include a safety protection feature that discontinues the electrical stimulation of a pancreas-related sympathetic nerve in the following exemplary events: abnormal operation of the implantable system 116 (e.g. overvoltage); abnormal readout from an implanted physiological sensor 111 (e.g. temperature increase of more than 2 degrees Celsius or excessively high or low electrical impedance at the electrode-tissue interface); abnormal readout from an external body-worn physiological sensor 121 (not shown); or abnormal response to stimulation detected by a user or an operator (e.g. a physician). The safety precaution feature may be implemented via controller 101 and communicated to the implantable system 116, or internally within the implantable system 116.

The external system 118 may comprise an actuator 120 (not shown) which, upon being pressed by a user (e.g. a physician or the subject), will deliver a signal, via controller 101 and the respective communication subsystem, to trigger the microprocessor 113 of the implantable system 116 to deliver a signal to the nerve by the electrode 108.

System 100 of the invention, including the external system 118, but in particular implantable system 116, is preferably made from, or coated with, a biostable and biocompatible material. This means that the device/system is both protected from damage due to exposure to the body's tissues and also minimizes the risk that the device/system elicits an unfavorable reaction by the host (which could ultimately lead to rejection). The material used to make or coat the device/system should ideally resist the formation of biofilms. Suitable materials include, but are not limited to, poly(p-xylylene) polymers (known as Parylenes) and polytetrafluoroethylene.

The implantable device 116 of the invention will generally weigh less than 50 g.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Unless otherwise indicated each embodiment as described herein may be combined with another embodiment as described herein.

BRIEF DESCRIPTION OF THE DRAWINGS

FIG. 1 shows pancreatic nerve anatomical, electrophysiological and functional characterization in mice. FIG. 1B shows CAP recordings (left) and amplitudes (right) in the indicated tissues after pancreatic nerve electrical stimulation in a representative mouse (n=7). Mean+/−s.e.m. FIG. 1C shows epifluorescence images of whole mounted samples of the indicated tissues in td-TomatoTH-Cre mice (n=5). FIGS. 1D and 1E shows the impact of pancreatic nerve electrical stimulation on surface pancreatic blood flow measured by laser speckle. Representative color-coded images (FIG. 1D) and quantification (FIG. 1E) before, during and after pancreatic nerve electrical stimulation (450 µA, 10 Hz, 15 sec) (n=7). Quantification was performed in the area delineated by a dotted line.

FIG. 2 shows visualization and electrophysiological characterization of catecholaminergic fibers in pancreatic lymph nodes (LN). FIG. 2B shows FAPs (left) and peak amplitudes as a function of PNES intensity (right) (n=4). FIG. 2C shows the impact of successive PNES on FAP. Representative FAPs (left) and quantification of peak amplitude reduction as a function of PNES frequency (right) (n=4).

FIG. 3 shows tissue-specific impact of PNES on immune cell number and function in pancreatic LN. FIG. 3A shows the impact of PNES (450 µA, 10 Hz, 2 mn, 3 times, 3 hours apart) on lymphocyte numbers in pancreatic draining and non-draining LNs (n=14).

FIG. 4 shows the effect of PNES on glycaemia, β cell proliferation and insulitis in NOD mice. FIGS. 4A to 4D show recently diabetic NOD mice (n=10) were implanted with micro-cuff electrodes. When glycaemia reached 200 mg/dl, PNES (left) or sham electrostimulation (right) were applied (450 µA, 10 Hz, 2 mn) for 4-5 days three times a day. Glycaemia in diabetic NOD mice following PNES and sham electrostimulation. Representative mice (FIG. 4A) and glycaemia increase (n=10) (FIG. 4B) over a two month-period following PNES and sham electrostimulation. FIGS. 4C and 4D show glycaemia over a 4 days-period following individual sessions of PNES and sham electrostimulation. Unpaired (FIG. 4C) and paired representations (FIG. 4D). FIG. 4F shows representative confocal images (left) of pancreatic sections following insulin (red) and BrdU (green) staining (left), and number of BrdU+ insulin+ cells per islet (right) (n=6).

FIG. 8 is a block diagram illustrating elements of a system for performing electrical stimulation in a pancreas-related sympathetic nerve according to the present invention.

MODES FOR CARRYING OUT THE INVENTION

Experimental Study 1

Several nervous pathways including the sympathetic nervous system (SNS) inhibit inflammation [12]. The main SNS neurotransmitters are norepinephrine (NE) and epinephrine (E) that bind both α- and β-adrenergic receptors (AR), among which β2-AR are expressed by most immune cells

[13]. The control of inflammation by SNS leads to the vision of a new class of treatments known as bioelectronic medicines based on the modulation of the electrical signaling patterns of these nerves to treat inflammatory diseases [14].

Type 1 diabetes (T1D) is an autoimmune disease that results from the destruction of insulin-producing pancreatic β cells by autoreactive immune cells [1]. Like other visceral organs, the pancreas is innervated by nerves of the autonomous system including the SNS, which contributes to the control of glycaemia [3]. This study aims to identify a way for the use of bioelectronic medicine to inhibit disease progression in T1D patients.

Methodology

Mice were obtained through Jackson Laboratory (RIP-OVA high) or Charles River (NOD, C57/BL6, OT-I). All mice were females used between 6 and 12 weeks of age. The RIP-OVA high transgenic mice[9] express OVA in pancreatic islets and the OT-I transgenic mice express a TCR-specific for the H2Kb restricted (SIINFEKL) epitope of OVA [15]. All animal breeding and experiments were performed under conditions in accordance with the Inserm and European Union Guidelines. All animal experimental protocols received a local and national committee approval.

Figure 2D:
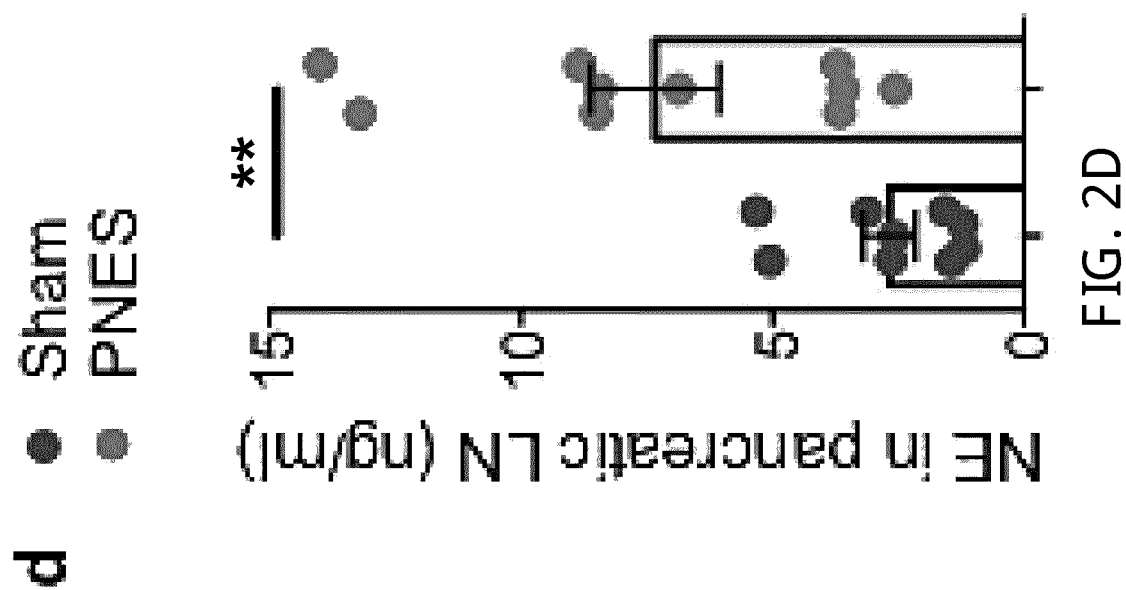
FIG. 2D shows NE content following PNES (450 µA, 10 Hz) or sham electrostimulation (n=10). Mean+/−s.e.m.
Figure 3B:
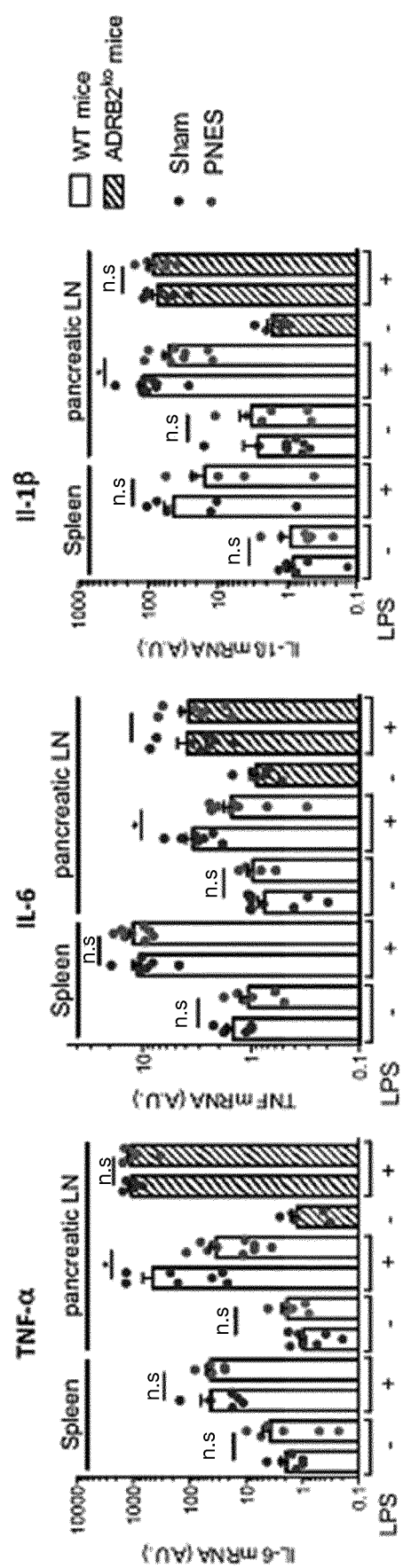
FIG. 3B shows the impact of PNES (450 µA, 10 Hz, 2 mn, 3 times, 3 hours apart) on LPS-induced cytokine mRNA levels in draining LNs and spleen (n=8).
Figure 3C:
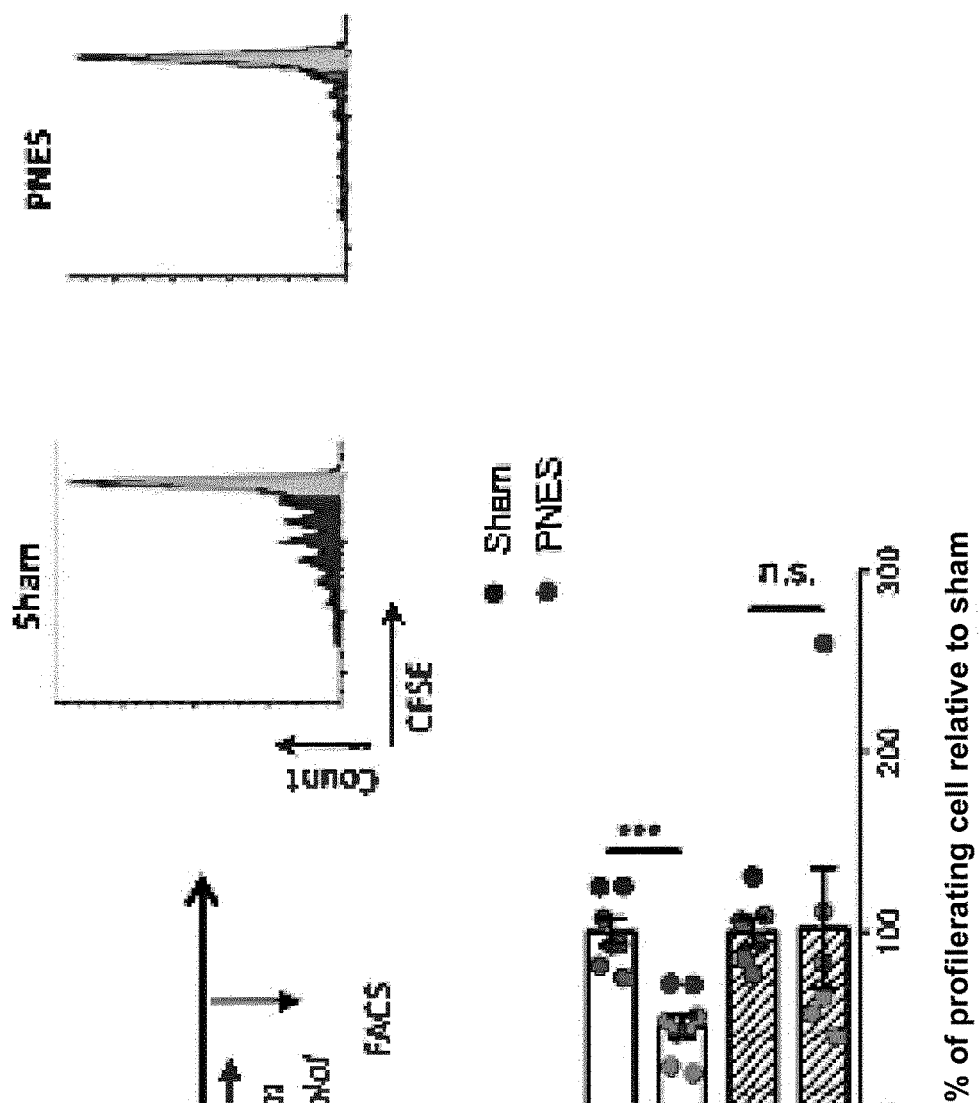
FIG. 3C shows a schematic representation of the experimental protocol used for assessing PNES (450 µA, 10 Hz, 2 mn, 3 times/day) impact on pancreatic auto-antigen cross-presentation (left). Representative FACS profiles of CFSE-labeled CD8+ OVA-specific T cells following PNES and sham electrostimulation (n=7) (middle). T cell proliferation relative to sham electrostimulated mice in mice treated or not with propranolol (right). Mean+/−s.e.m.
Figure 4C:
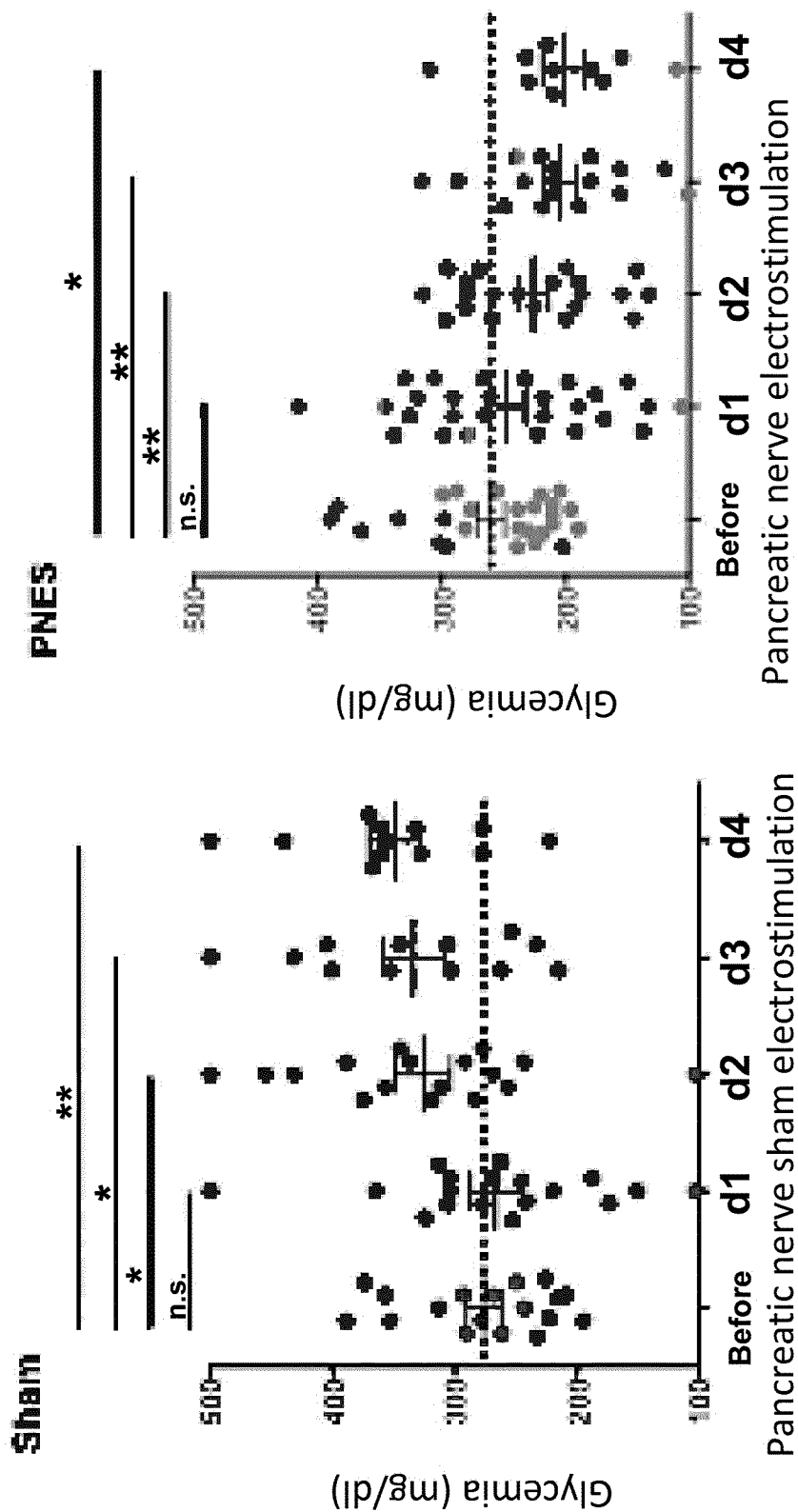
Figure 4D:
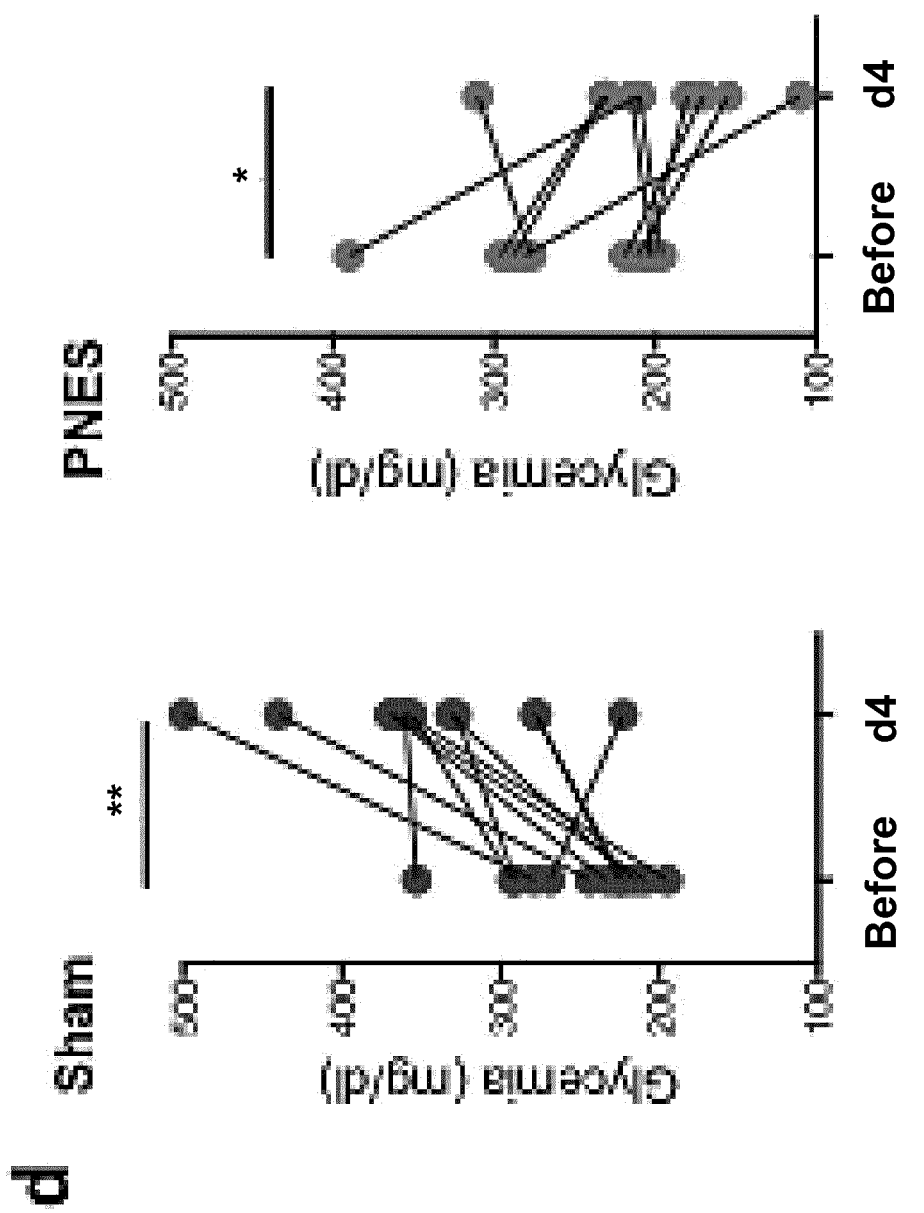
Figure 4G:
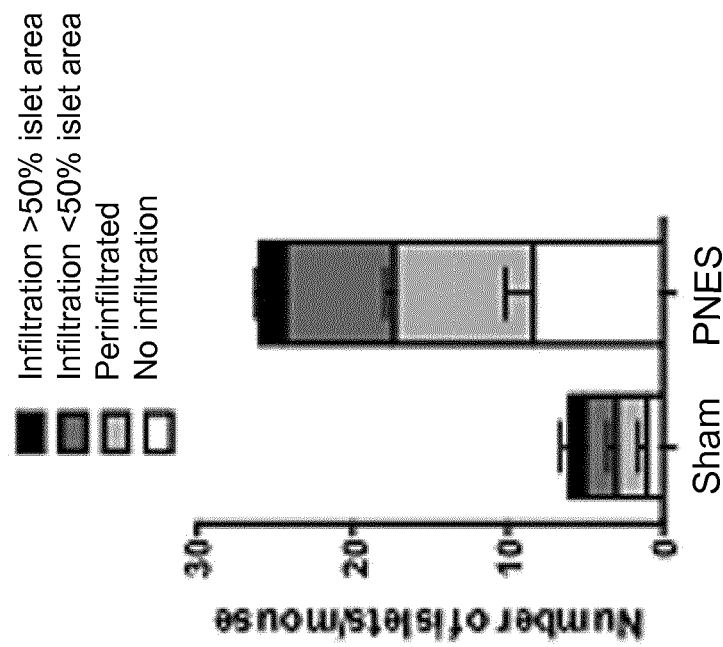
FIG. 4G shows the proportion of islets exhibiting severe, mild and low immune cell infiltration two weeks after PNES and sham electrostimulation (n=3). Mean+/−s.e.m.
Figure 4E:
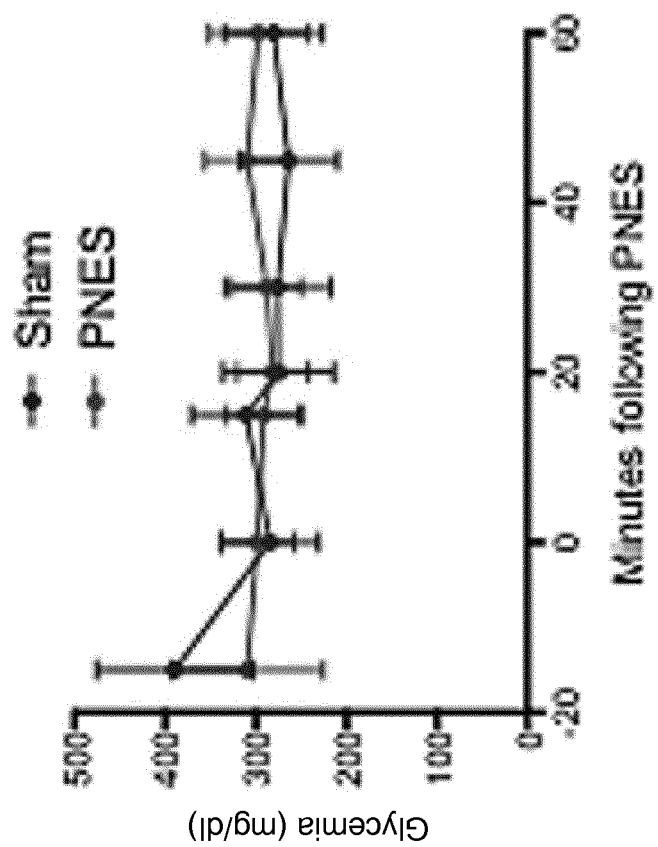
FIG. 4E shows short-term glycaemia in diabetic NOD mice following PNES and sham electrostimulation.

For acute electrostimulations (see FIGS. 1B, 1D and 2D) animals were anesthetized with a mixture of Ketamine (75 mg/kg) and Xylazine (60 mg/kg) i.p. and a hook electrode was placed under the pancreatic nerve and artery. For chronic experiments (see FIGS. 3 and 4) animals were anesthetized with isofluorane and the area around the right abdominal artery next to the kidney was exposed. A 1 mm length 100 μm sling micro-cuff electrodes were implanted (CorTec) onto the pancreatic nerve after isolation. The wires were maintained in place by a stitch point placed on the abdominal muscles and exited abdominally. To avoid animal scraping, the abdomen was wrapped with bandages. A morphinic derivative was given before and after the surgery (Buprecare®, 0.1 mg/kg, i.p. 30 minutes before surgery and 0.05 mg/kg, s.c. after surgery and the following 2 days).

After placing a hook electrode onto the pancreatic nerve and artery, platinum-recording electrodes were placed onto the pancreatic nerve, pancreatic lymph nodes (LN), pancreas tissue and liver for recording of CAP with wireless 100-system (Multi Channel System). Reference was placed in the nearby tissue.

After placing a hook electrode onto the pancreatic nerve and artery, platinum-iridium recording electrodes (Phymep) were placed onto the pancreatic nerve, pancreatic LN, pancreas tissue and liver for CAP recording using a wireless recording system (W8, Multi-Channel Systems). Ground/Reference wires were placed into the nearby tissue. For FAP, recordings were performed on explants from tdTomatoTH-Cre that were placed in a recording chamber at room temperature (20-25° C.) superfused at a flow rate of 1 ml min-1 with oxygenated artificial cerebrospinal fluid (ACSF) under an upright microscope (Zeiss) equipped with infrared video camera (Axiocam, Zeiss) and fluorescence. The pancreatic nerve was introduced into a suction-stimulating electrode connected to a STG 4002 stimulator (Multichannel system) piloted by MC-stimulus program (Multichannel systems). Square pulses of 1 ms and intensities ranging from 10-1500 μA were used for stimulation. Recordings were made using pipettes made from borosilicate glass capillary (Hilgenberg) with resistance of 3-6 MΩ when filled with extracellular solution, placed near red fluorescent axons. Signals were amplified using an Axopatch 200B (Axon Instruments), digitized at 10 kHz via an Digidata 3200 interface (Molecular devices) controlled by pClamp10.0 software (Molecular Devices) and digitally filtered at 3 KHz. All recordings were performed in a Faraday cage.

All recordings were performed in Faraday cage.

For experiments on anesthetized animals, Master-8 (A.M.P.I.), PlexStim V2.3 (Plexon) and STG 4002 stimulator (Multichannel system) were used respectively for CAP, pancreatic blood perfusion and FAP recording. For all experiments on conscious animals, mice were placed in individual cage and connected to a PlexStim V2.3 (Plexon) stimulator. Unless specified, the set-up of the electrostimulation were rectangular charged-balanced biphasic pulses with 450 μA pulse amplitude, 2 ms pulse width (positive and negative) at 10 Hz frequency for 2 minutes.

To measure norepinephrine levels, pancreatic LN were harvested and snap-frozen in liquid nitrogen immediately after electrostimulation. The organ was processed and NE was measured by ELISA (DLD Diagnostika GmbH) according to manufacturer recommendations.

For flow cytometry, single-cells suspensions were stained with anti-CD45 (clone 30F11), anti-CD3 (17A2), anti-CD4 (RM4-5), anti-CD8a (53-6.7), anti-CD19 (1D3). All antibodies are from BD Biosciences. Dead cells were excluded using 7-AAD staining. Data were acquired on SP6800 (Sony) flow cytometer and analyzed using Kaluza software.

RT-PCR and Q-PCR. RNA from pancreas were isolated following manufacturers instruction (miRNEasy micro kit, Quiagen) after mechanical dissociation using Lysing Matrix D tubes (FastPrep, MP biomedical). RNA quantitiy and quality were analyzed with Nanodrop and equivalent amount of RNA were used to perform RT-PCR using QuantiTect Reverse transcription kit (Quiagen). Quantitative PCR were performed using SyberGreen Master Kit (Roche) and LightCycler 480 II (Roche). Primers were designed according to PrimerBank (Harvard University). mRNA cytokine expression were normalized to GAPDH using LightCycler software (Roche).

Glycaemia was monitored using a Free Style Papillon Vision (Abbott) taking a blood drop (<10 μl) from the tail.

For laser speckle, after anesthesia, the pancreas tissue was exposed and the animal was placed on a heating blanket that was kept at 30-32° C. The pancreas was placed about 30 cm below the Moor-FLPI laser speckle perfusion (LSP) imager (Moor instruments Ltd.). The scanning model was of low density and 25 fps, the time interval was 1 s, exposure time was 20 ms, and 10 frames were continually scanned at each time point (10 frames were averagely processed into a single frame to obtain the mean pancreatic blood perfusion at each time point). Then the pancreatic blood perfusion images were saved and analyzed by the Image Review Program of Moor-FLPI-V2.0 software. The round region of interest (ROI) with the same area in each LSP image was selected for measuring the pancreatic blood perfusion.

In histogram analysis, removed pancreas were fixed in 10% neutral formalin for 24 hrs, dehydrated with alcohol, embedded in paraffin and sectioned in 8 μm thickness with microtome. Then, section was stained with hematoxylin and eosin, and the grade of insulitis was evaluated under light microscope. The extension of insulitis was determined as the percentage of normal, peri-infiltrated, infiltration of <50% of islet area, or infiltration of >50% of islet area.

For statistical analysis, the student t-test (see FIGS. 2D, 3C, 4B, 4C and 4D) or Mann-Whitney test (FIGS. 2D, 3A, 3B and 4F) were performed to calculate statistical differences of Gaussian and non-Gaussian distributed data respectively.

Results and Discussion

Figure 1A:
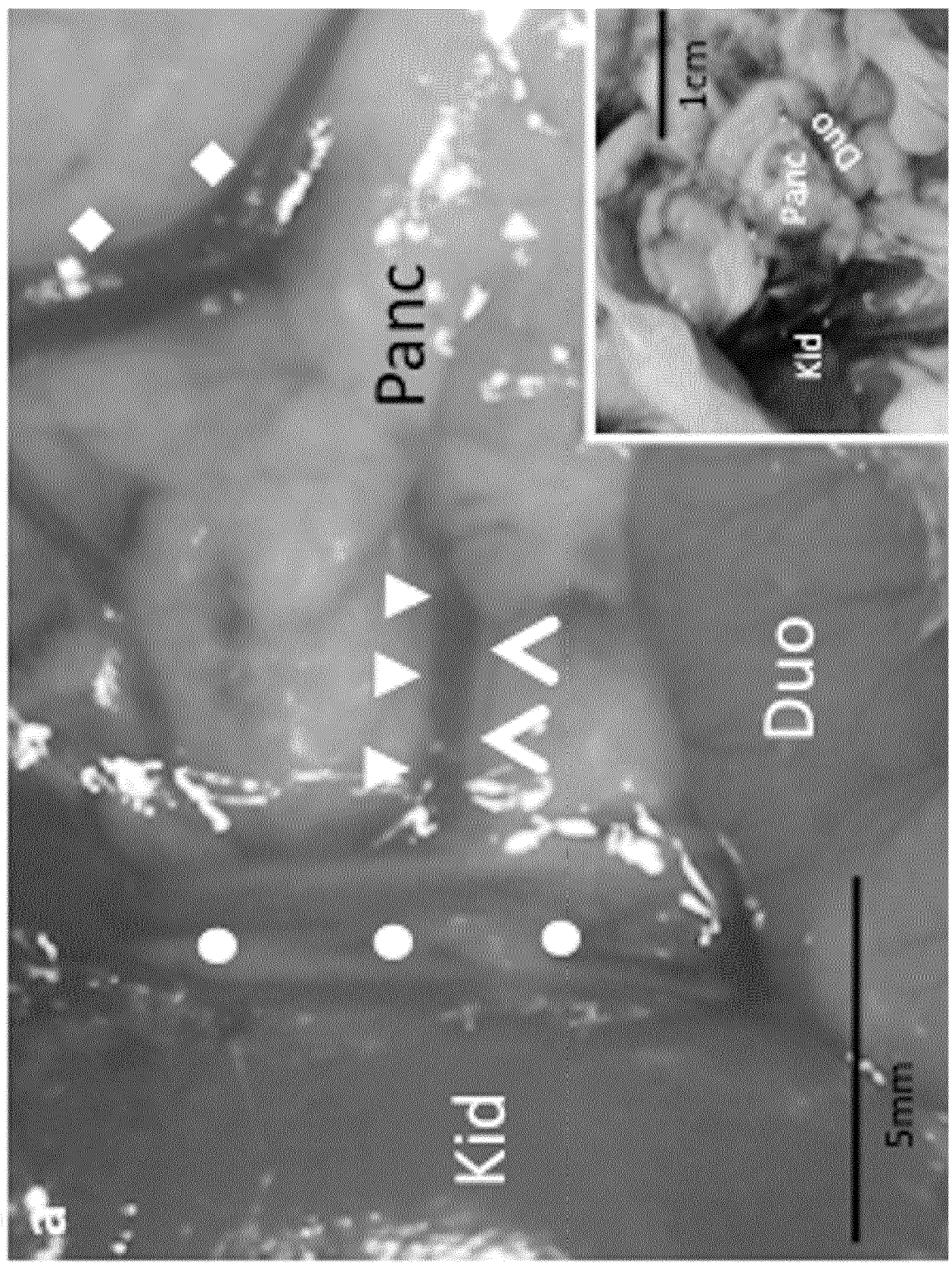
FIG. 1A shows images of pancreatic nerve gross anatomy showing pancreatic artery and blood vessels visualized by Blue Evans injection (right). Kidney (Kid), duodenum (Duo), pancreas (Panc), pancreatic (full arrow head) and abdominal (circles) arteries, pancreatic vein (diamond) and nerve (empty arrow head).
Figure 2A:
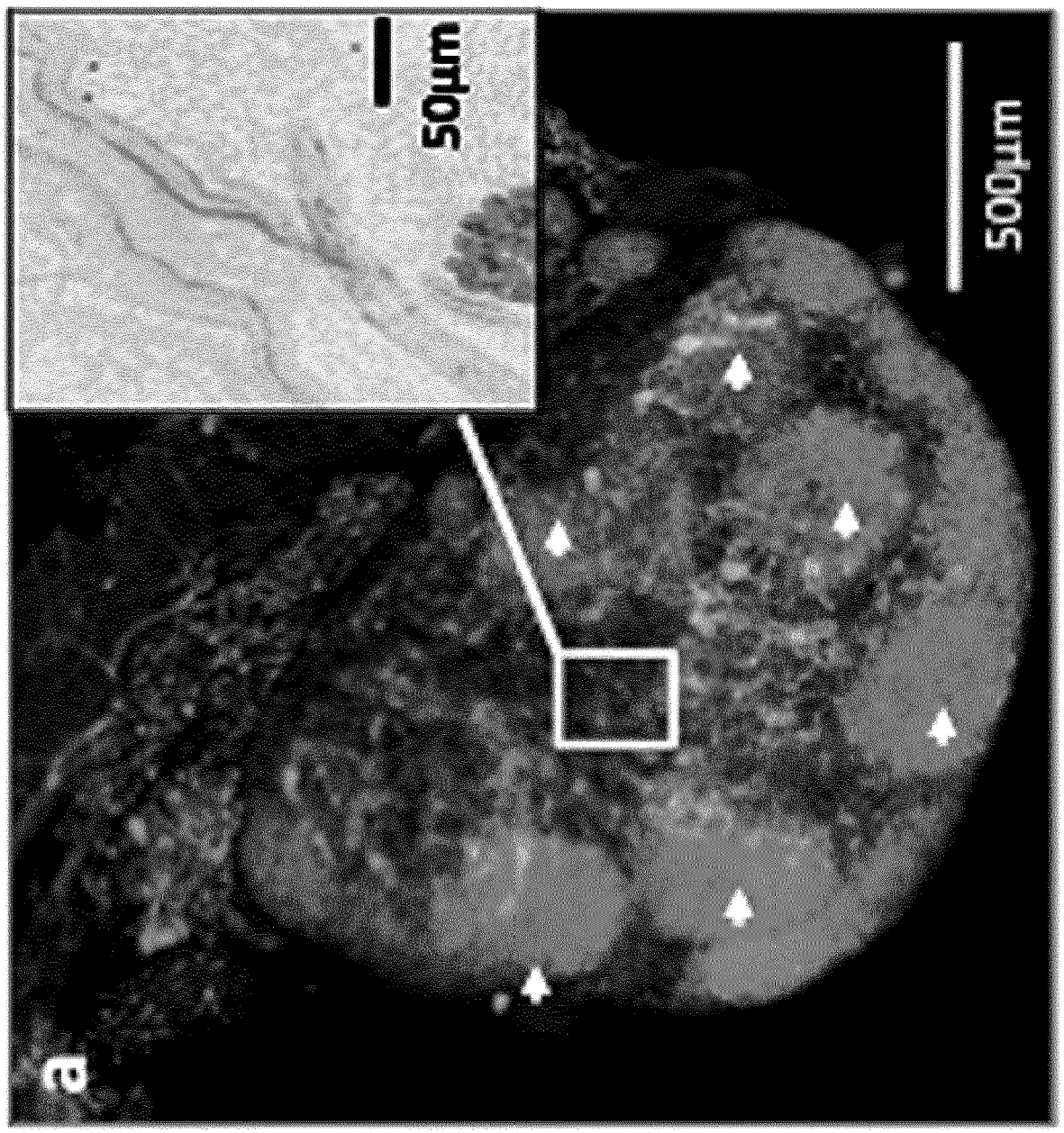
FIG. 2A shows confocal fluorescence image of whole mounted pancreatic LN from tdTomatoTH-Cre mice after injection of Alexa-647-conjugated Wheat Germ Agglutinin (WGA) at low and high magnification. B cell follicles which exhibit a red fluorescence as the result of TH expression in B cells are indicated by arrowheads.
Figure 2B:
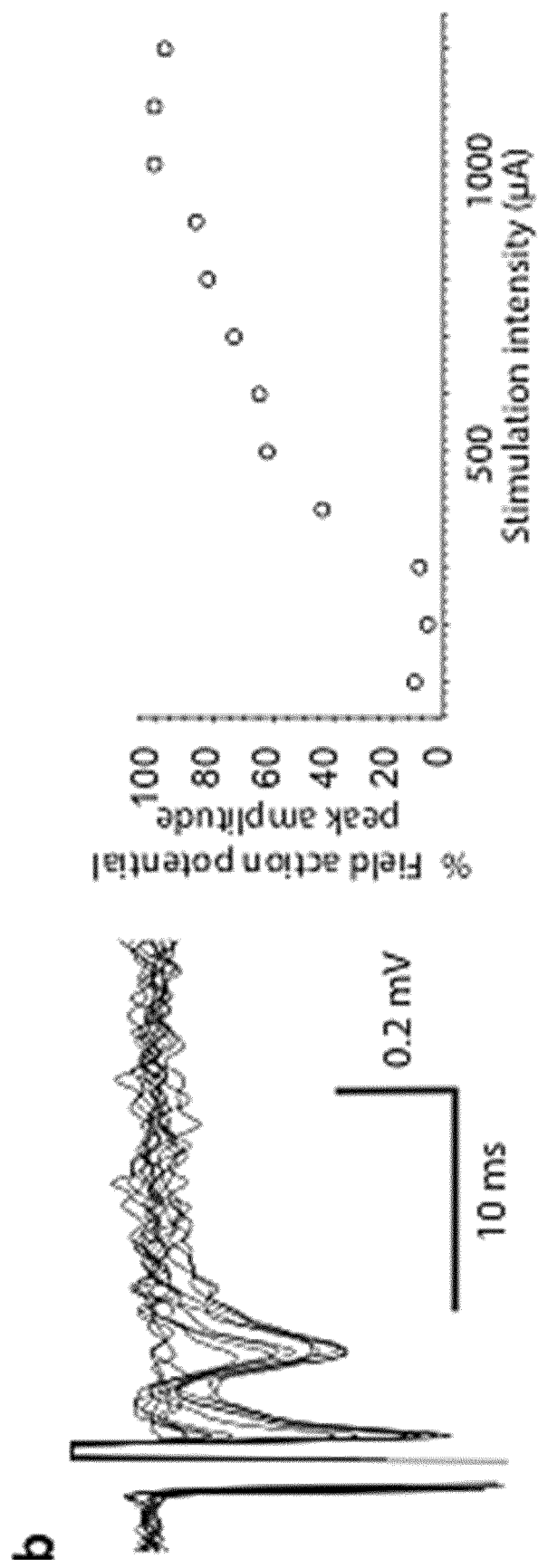
FIGS. 2B and 2C show recordings of fluorescent axons electrical activity in the pancreatic LN of tdTomatoTH-Cre mice following pancreatic nerve electrical stimulation (PNES). In particular.
Figure 2C:
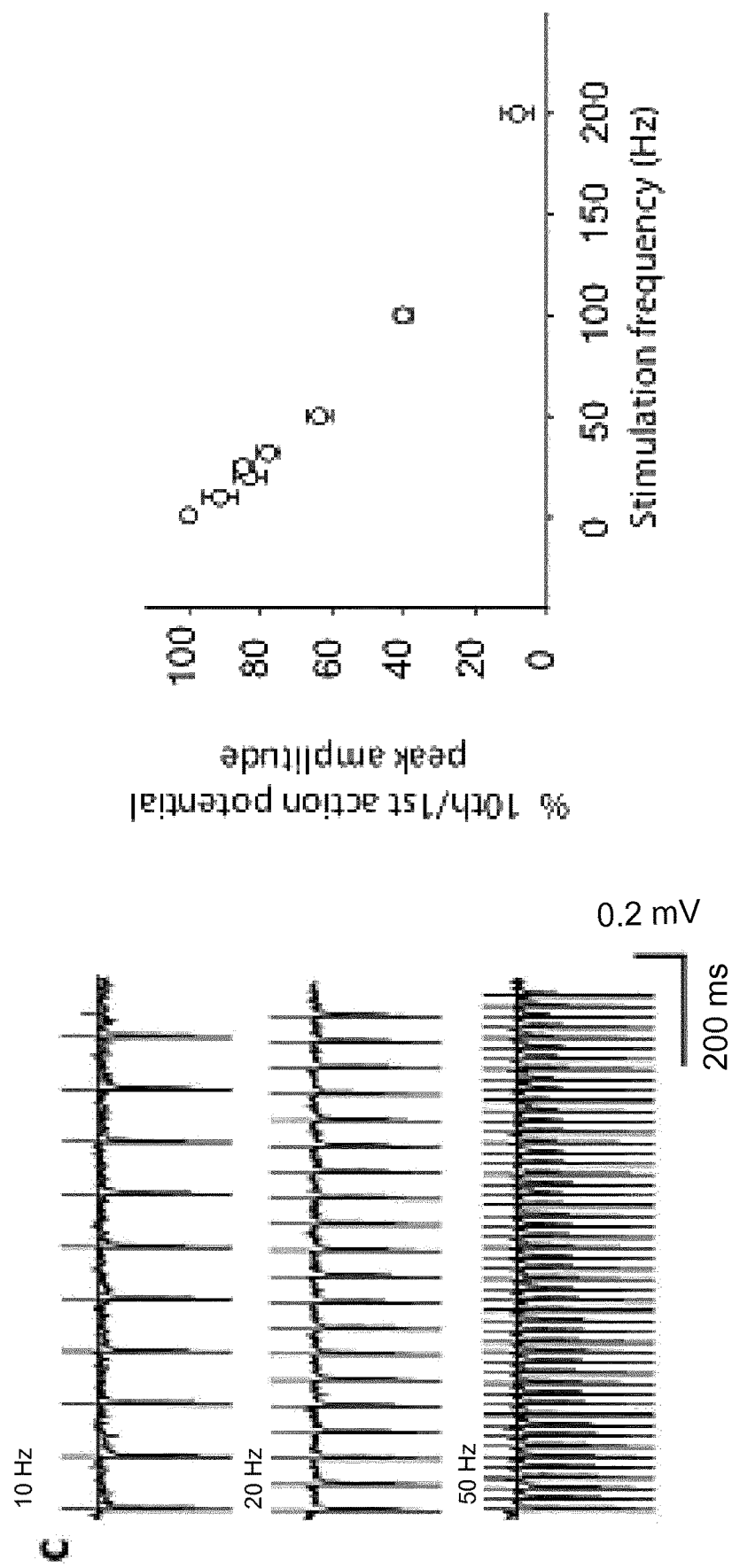
Figure 5:
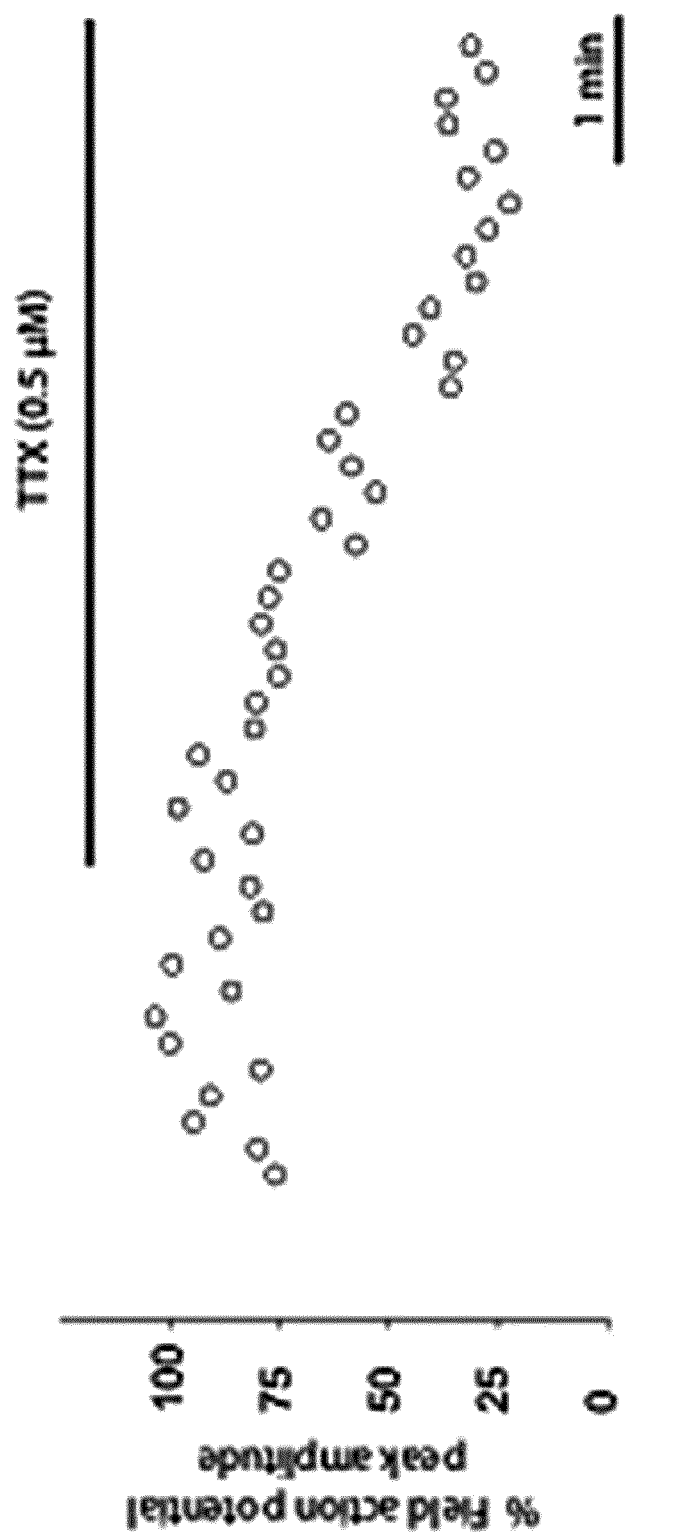
FIG. 5 shows recordings of fluorescent axons electrical activity in the pancreatic LN of tdTomatoTH-Cre mice following PNES (800 µA, 0.1 Hz). Peak amplitudes following addition of Tetrodotoxin (TTX) to the medium.

Gross anatomy of the pancreatic region in C57BL/6 mice showed a single artery (diameter 500 μm) branching from the abdominal artery, supplying blood to the pancreas head and part of the duodenum, and associated with a 50 μm-diameter nerve-like structure (see FIG. 1A). To confirm that this structure was a nerve and to identify the innervated tissues, a hook electrode was placed onto it and a recording electrode on visceral tissues. Electrostimulation was applied and Compound Action Potentials (CAPs) were recorded in pancreatic lymph nodes (LNs) and pancreas head, but not in liver (FIG. 1B). To investigate whether this nerve was catecholaminergic, fluorescent reporter tdTomatoTH-Cre transgenic mice carrying the tdTomato fluorescent protein gene downstream the tyrosine hydroxylase (TH) gene promoter were used. Pancreatic nerve-like structures exhibited red fluorescence in tdTomatoTH-Cre, demonstrating that they contained catecholaminergic fibers (see FIG. 1C). In agreement with the ability of the SNS to induce vasoconstriction, high frequency and amplitude electrical stimulation (20 Hz, 1 mA) reduced pancreatic blood flow when applied to the pancreatic nerve (see FIG. 1D). Red fluorescent axons were also evidenced in the pancreatic LN medulla zone further confirming that these nerves did not only project to the pancreas itself, but also to the LNs that drained this tissue (see FIG. 2A). To electrophysiological characterize the catecholaminergic fibers projecting to pancreatic LN, the pancreatic nerve was placed into a suction electrode and Field Action Potentials (FAP) of red fluorescent fibers within this LN were recorded using a microelectrode (see FIG. 2B). FAP were readily detected when PNES intensity was above 400 μA (see FIG. 2B) and inhibited by tetrodotoxin (TTX) treatment (see FIG. 5). Exhaustion of axonal excitability was detected when frequency was above 10 Hz (FIG. 2C) suggesting that this nerve contained unmyelinated postganglionic fibers [16].

For peripheral nerve electrostimulation to be used for therapeutic intervention, electrical parameters need to be adjusted in order to minimize off-target effects while allowing release of therapeutic levels of neurotransmitters. To identify such parameters, different amplitudes and frequencies were tested and eventually identified parameters (10 Hz, 450 μA) that did not reduce pancreatic blood flow (see FIG. 1D) while increasing norepinephrine (NE) levels in pancreatic LNs (see FIG. 2D).

Based on these results, these parameters were used for the rest of the study.

Figure 6:
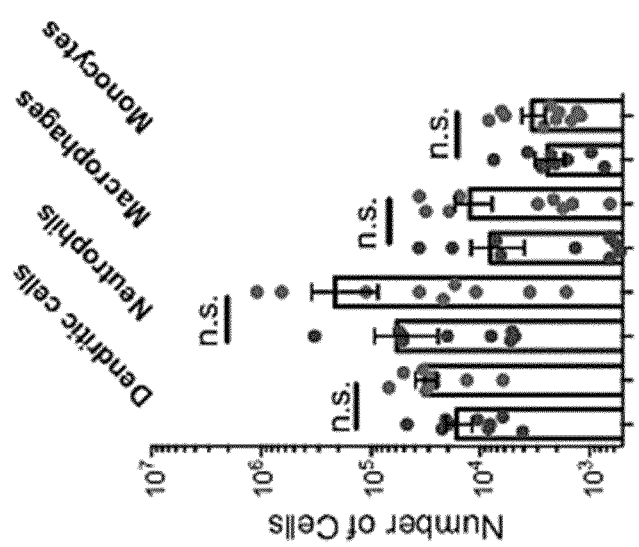
FIG. 6 shows the impact of PNES on myeloid cell number in pancreatic LN. Myeloid cell numbers in the pancreatic draining LNs following PNES (450 µA, 10 Hz, 2 mn, 3 times, 3 hours apart) (n=9). Mean+/−s.e.m.

Next, the impact of PNES on immune cell number and activation in pancreatic LNs were investigated. Because drugs used for anesthesia interfere with physiology and more specifically immunity, a minimally traumatic surgical procedure for chronically implantation of micro-cuffs electrodes onto the pancreatic nerve was developed allowing experiments in conscious animals. Compared to sham-stimulated mice, stimulated mice exhibited higher number of T and B-lymphocytes, but not myeloid cell types (see FIG. 6), in pancreatic draining but not non-draining LNs (see FIG. 3A). This latter result is consistent with the role of β2-AR in lymphocyte egress from LN [17]. PNES also reduced LPS-induced pro-inflammatory cytokine mRNA levels in pancreatic LN but not spleen (see FIG. 3B). In agreement with the role of β2-AR in antigen cross-presentation [18], PNES inhibited pancreatic auto-antigen cross-presentation as shown by reduced proliferation of adoptively transferred OVA-specific CD8+ TCR transgenic T-cells in RIP-OVA transgenic mice that selectively expressed OVA in pancreatic islet β cells (see FIG. 3C). The effects of PNES on both immune cell accumulation and LPS-induced pro-inflammatory cytokine mRNA production in draining LNs were abolished in β2-AR−/− mice demonstrating that they were mediated by the binding of NE to β2-AR (see FIG. 3A and FIG. 3B). Further experiments using β1/β2 adrenergic receptor antagonist propranolol showed that the effect of PNES auto-antigen cross-presentation was β-AR-dependent (see FIG. 3C).

The impact of PNES on T1D progression was investigated in Non-Obese-Diabetic (NOD) mice that spontaneously develop insulitis and autoimmune diabetes between 3 and 6 months of age. Female NOD mice were monitored daily for hyperglycaemia and recently diabetic mice were implanted with micro-cuff electrode onto the pancreatic nerve (n=16). After surgical recovery, PNES was applied or not as soon as glycaemia reached 200 mg/dl three times a day for 3-4 days. Glycaemia increased more slowly in mice submitted to PNES sessions over more than a month compared to sham-electrostimulated animals (see FIG. 4A and FIG. 4B). A beneficial impact of PNES on glycaemia was evidenced as early as two days after session initiation (see FIG. 4C). On day 4, 80% of electrostimulated mice showed a decrease in glycaemia compared to 10% in sham-stimulated animals (see FIG. 4D).

Figure 7:
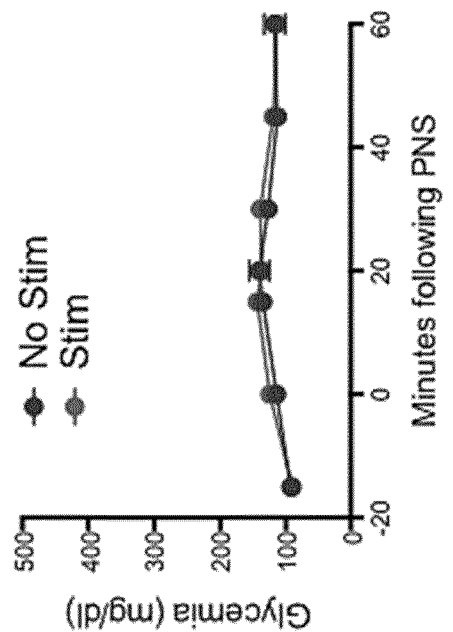
FIG. 7 shows the short-term effect of PNS on hyperglycaemia in fed (left panel) and fasted (right panel) in non-diabetic (A) and recently diabetic (B) NOD mice. Mean+/−s.e.m.

Several underlying mechanisms could account for the beneficial impact of PNES on glycaemia including a direct increase of insulin production by β cells, the induction of islet β cell proliferation and a reduced inhibitory effect of infiltrating immune cells on β cell activity. PNES did not have any impact on glycaemia in diabetic or non-diabetic mice for up to one hour suggesting that it did not directly induces insulin production (see FIG. 4E and FIG. 7). To investigate the impact of PNES on pancreatic β-cell proliferation, mice implanted with micro-cuff electrodes and submitted to PNES for 5 days while receiving BrdU. Quantification of BrdU+ insulin-secreting cells showed no significant difference between PNES group and sham-electrostimulated group suggesting that PNES did not induce β cell proliferation (see FIG. 4F). In contrast, insulitis was reduced in stimulated mice compared to sham-stimulated mice when analyzed 15 days after PNES initiation (see FIG. 4G).

Conclusion

In summary, the inventors identified a catecholaminergic nerve that projects to the pancreatic lymphatic system (e.g. LN) and demonstrated that electrostimulation of this nerve inhibited T1D progression in NOD mice with minimal off target effects. The beneficial impact of PNES on glycaemia was likely be immune-mediated as suggested by reduced levels of pro-inflammatory cytokines and accumulation of lymphocytes in pancreatic LNs, reduced antigen cross-presentation and insulitis. Besides providing the proof-of-concept that electrical stimulation of a pancreas-related sympathetic nerve could be used to inhibit T1D progression, this study supports a new class of treatments known as bioelectronic medicines based on the modulation of the electrical signaling patterns of peripheral nerves to treat immune-mediated inflammatory diseases.

Experimental Study 2

Figure 9:
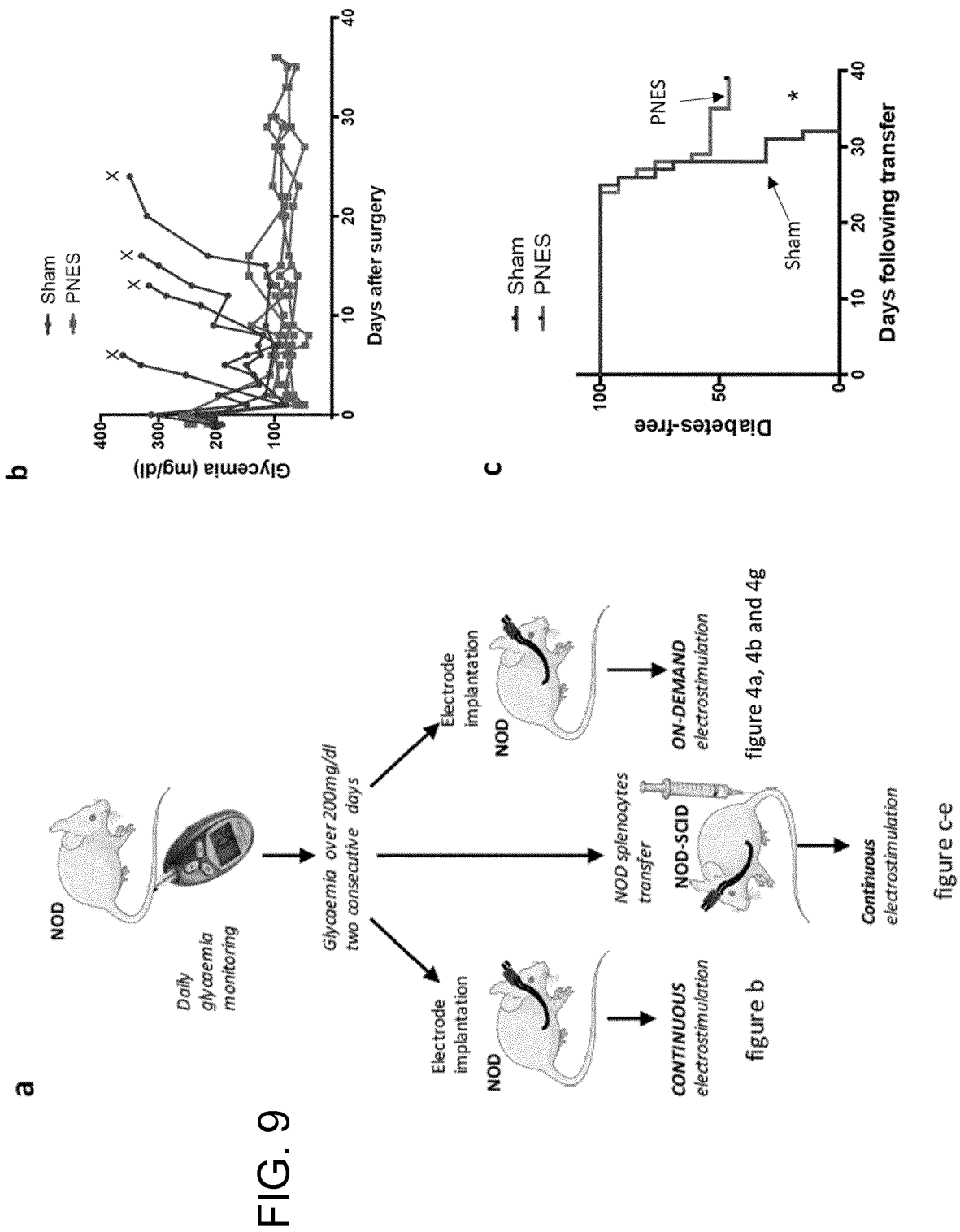
FIG. 9 shows the impact of continuous PNES on glycaemia and insulitis in NOD mice. (a) Schematic representation of the experimental protocol. (b) Glycaemia following continuous PNES in individual mice (n=4/group). (c) Diabetes incidence in NOD-SCID mice (n=13/group). (d) Number of islets per mouse and proportion of islets exhibiting severe, mild and low immune cell infiltration two weeks after PNES. Mean+S.E.M. (n=4/group). (e) Total number of cells (left panel) and number of B, $CD4^+$ and $CD8^+$ T cells (left panel) in pancreatic LNs two weeks after PNES. Mean+S.E.M. (n=5-6/group).
Figure 9:
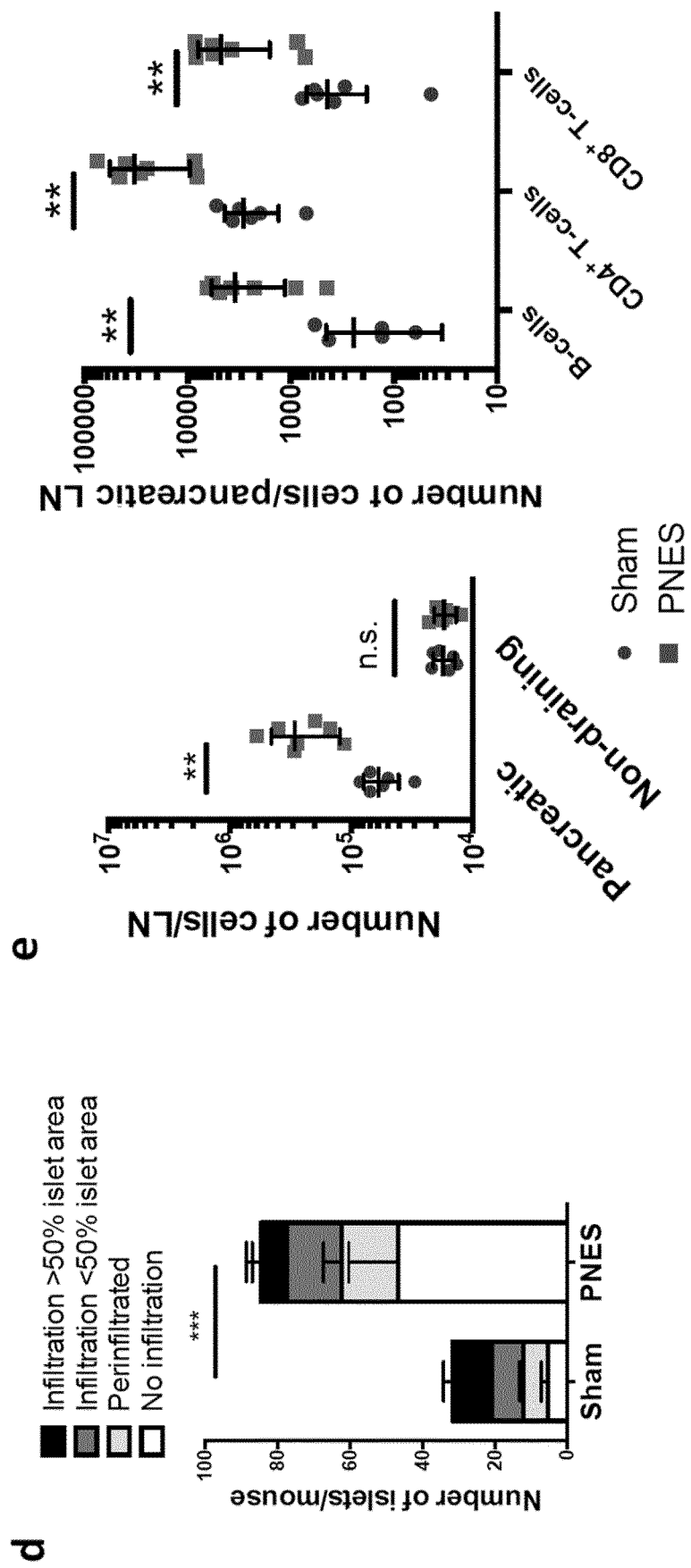

The impact of PNES on T1D progression in NOD mice that spontaneously develop autoimmune diabetes between 3 and 6 months of age was next investigated. Once diagnosed with diabetes, NOD mice were implanted with a micro-cuff electrode onto the pancreatic nerve and PNES was applied one day later three times a day for 6 weeks (FIG. 9a).

Methodology

Mice

C57BL/6, NOD, NOD-SCID and OT-112 mice were purchased from Charles River. RIP-mOVA13, tdTomatoTH-Cre 14, 15 and ADRB2ko mice were purchased from The Jackson Laboratory and backcrossed on the C57BL/6 background for at least 10 generations. All experiments were performed with female 8-12 wk old mice unless otherwise indicated. Mice were housed on a 12 hours light/dark cycle (lights on/off at 7 am/7 pm) with food ad libitum. All animal breeding and experiments were performed under conditions in accordance with the Inserm and European Union Guidelines. All animal experimental protocols received a local and national committee approval.

Electrodes and Surgery

For studies in anaesthetized animals, mice were anaesthetized by an intraperitoneal injection of a mixture of ketamine (75 mg/kg) and xylazine (60 mg/kg) and a hook electrode was placed under the pancreatic nerve. For studies in conscious animals, mice were anaesthetized with isoflurane and the area around the right abdominal artery next to the kidney was exposed. One mm length 100 µm-sling micro-cuff electrodes (CorTec) were implanted onto the pancreatic nerve.

Electrostimulation

Mice were placed in individual cage and connected to either a PlexStim V2.3 (Plexon) or MAPS (Axonic) stimulator. Unless specified, the set-up for electrostimulation were rectangular charged-balanced biphasic pulses with 450 gA pulse amplitude, 2 ms pulse width (positive and negative) at 10 Hz frequency for 2 minutes.

Adoptive Cell Transfer into NOD-SCID Mice

Splenocytes from overtly diabetic NOD mice were prepared and injected intravenously into 6 wk-old NOD-SCID mice ($5 \times 10^6$ cells/mouse).

Glycaemia

Glycaemia was monitored using a Free Style Papillon Vision (Abbott) on a blood drop (<10 µl) harvested from the tail. NOD and NOD-SCID mice were considered diabetic when glycaemia was >250 mg/di for two consecutive days.

Flow Cytometry

Single-cell suspensions were stained with anti-CD45 (clone 30F11), anti-CD3 (17A2), anti-CD4 (RM4-5), anti-CD8a (53-6.7), anti-CD19 (1D3). All antibodies were purchased from BD Biosciences. Dead cells were excluded using 7-AAD staining. Data were acquired on a SP6800 (Sony) flow cytometer and analyzed using the Kaluza software.

Statistics

Diabetes progression was plotted using Kaplan-Meier's curves and differences between groups were estimated using the log-rank test. Normality of sample distribution was assessed using the Kolmogorov-Smirnov test. For comparison between two groups, statistical significance was assessed using paired or unpaired Student's t-test or the Mann-Whitney U-test as appropriate. For comparison between more than groups, statistical significance was assessed using one-way ANOVA followed by Tukey's post hoc test. All statistical analysis were performed using GraphPad Prism v.6.

Results and Discussion

Figure 10:
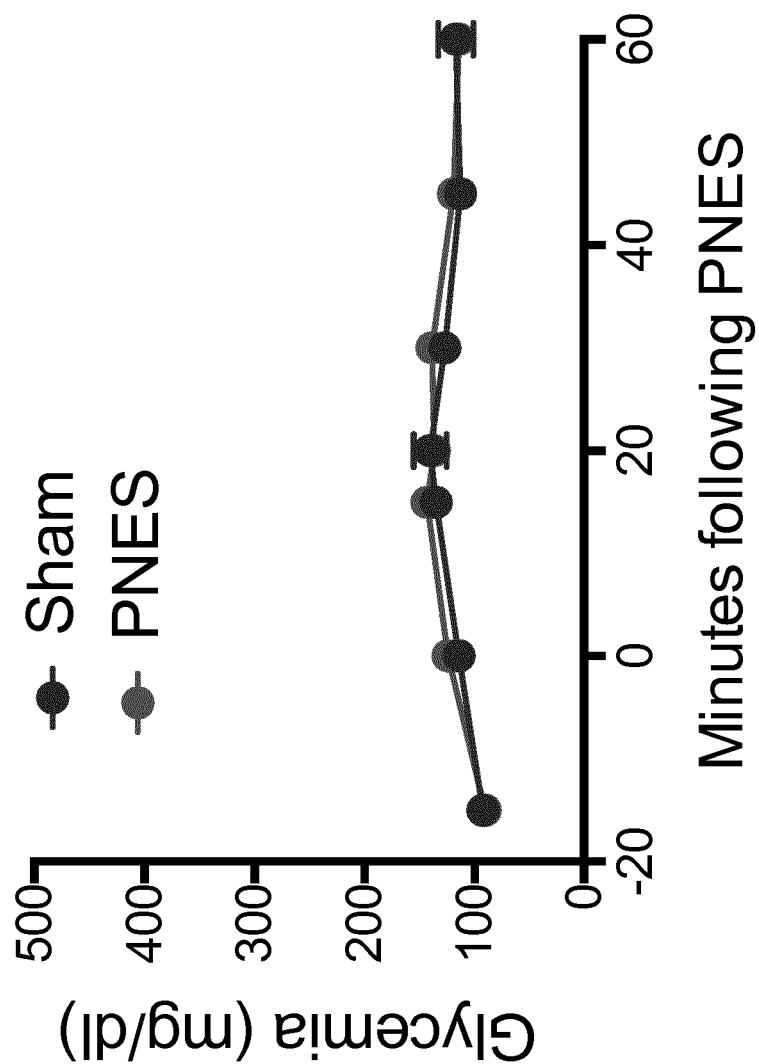
FIG. 10 shows the impact on glycaemia up to one hour post-PNES in NOD mice.
Figure 11:
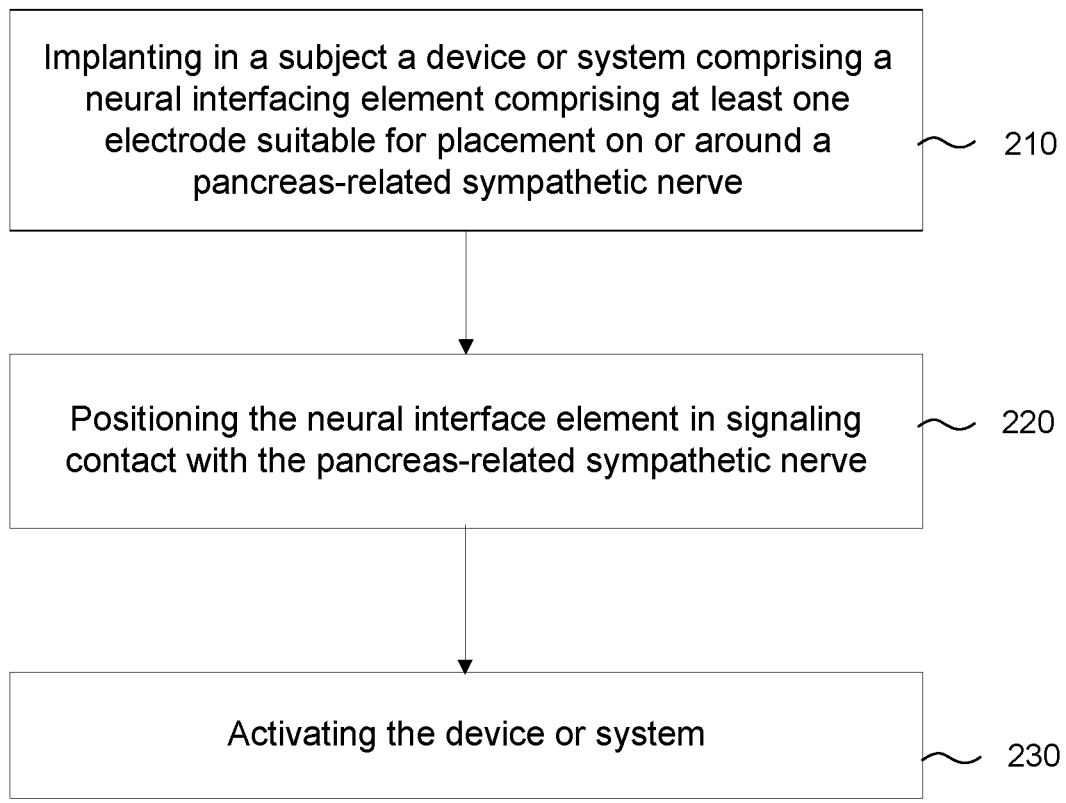
FIG. 11 is a flow chart showing an example method of reversibly modulating neural activity in a pancreas-related sympathetic nerve.

Mice returned to normoglycaemia after surgery, a phenomenon likely due to the anti-inflammatory effect of anesthetics [19-20]. However, while glycaemia started to increase again in sham stimulated mice resulting in full-blown diabetes, it remained below 150 mg/ml in PNES animals (FIG. 9b). PNES did not impact glycaemia in diabetic NOD mice for up to 1 hour suggesting that it did not directly impact insulin secretion (FIG. 10).

To investigate the underlying mechanisms of PNES-mediated protection, the inventors used the well-characterized synchronous model of T1D in which diabetogenic T cells from NOD mice are transferred into immune-deficient syngeneic NOD-SCID recipients [21]. While all (13 out of 13) sham stimulated mice developed T1D within 4 weeks after adoptive cell transfer, only 55% (7 out of 13) of PNES recipients did p=0.015, FIG. 9c). This shows that PNES inhibited T1D progression by acting on pathogenic effector T cells.

In another set of experiments, mice were sacrificed 2 weeks after adoptive cell transfer and analyzed for both insulitis and number of lymphocytes in pancreatic LNs. PNES mice had 2.7-fold as many islets than sham stimulated mice (84.5±20.3 versus 31.75±3.6, p=0.029) (FIG. 9d). In addition, the proportion of non-infiltrated islets was higher in PNES mice (55% versus 17.5%) (FIG. 9d). Furthermore, while PNES and sham stimulated mice exhibited similar number of lymphocytes in non-draining LNs, PNES mice had 4- to 5-fold more lymphocytes in draining LNs ($29.0 \pm 12.0 \times 10^4$ versus $6.0 \pm 1.5 \times 10^4$ per mouse, p=0.006), a result similar to what we had observed in C57BL/6 mice (FIG. 9e).

Conclusion

These results show that applying electrical stimulation to a non-vagal nerves could have therapeutic effects for the treatment or prevention of immune-mediated inflammatory disorders such as T1D.

REFERENCES

[1] Herold, K. C. (2013). The Lancet Diabetes & Endocrinology, 1(4):261-263.
[2] Herold, K. C. et al. (2013). Nature Reviews Immunology, 13(4):243-256.
[3] Ahren, B. (2000). Diabetologia, 43(4):393-410.
[4] Cesmebasi et al. (2014). Clinical Anatomy, 28(4):527-537.
[5] Accornero et al. (1977). J. Physiol., 273:539-560.
[6] Ayres et al. (2016). J. Neurophysiol., 116:51-60.
[7] Bruns et al. (2015). Neurology and Urodynamics, 34:65-71.
[8] Soltani, N, et al. (2011) PNAS, 108:11692-11697.
[9] Ben-Othman, N, et al. (2017). Cell, 168:73-85.
[10] Franke et al. (2014). J. Neural Eng., 11(5):056012.
[11] Duke et al. (2012). J. Neural Eng., 9(3):036003.
[12] Chavan, S. S. and Tracey, K. J. (2014). Nature Medicine, 20:239-241.
[13] Nance, D. M. & Sanders, V. M. (2007). Brain, Behavior, and Immunity, 21(6):736-745.
[14] Birmingham, K. et al. (2014). Nature Reviews Drug Discovery, 13(6):399-400.
[15] Hogquist, K. A. et al. (1994). Cell, 76(1):17-27.
[16] Duclaux, R. et al. (1976). Journal of Physiology, 260(2):487-495.
[17] Nakai et al. (2014). J. Exp. Med., 211(13):2583-2598.
[18] Herve, J. et al. (2013). Journal of Immunology: 190: 3163-3171.
[19] Lee, H, et al. (2007) Shock Augusta Ga, 27:373-379.
[20] Lee, H, et al. (2007). Am. J. Physiol. Renal. Physiol, 293:F713-722.
[21] Christianson, S, et al. (1993). Diabetes, 42:44-55.

The invention claimed is:

1. A device or system comprising:
a neural interfacing element comprising at least one electrode, suitable for placement on or around a pancreas-related sympathetic nerve of a subject, wherein the pancreas-related sympathetic nerve is a pancreas-related sympathetic nerve supplying a lymphatic system of the pancreas; and
a signal generator configured to generate a signal to be applied to the pancreas-related sympathetic nerve via the at least one electrode such that the signal reversibly modulates neural activity of the pancreas-related sympathetic nerve, wherein the signal inhibits T cell activation or migration to the pancreas to produce a change in a physiological parameter in the subject,
wherein the change in the physiological parameter is one or more of the group consisting of: an increase in blood insulin level, a reduction in (fasting) blood glucose level, a reduction in glycated hemoglobin (HbA1c) level, a reduction in inflammation systemically or locally in the pancreas, such as insulitis an increase in catecholamine levels in the pancreas, an increase in GABA levels in the pancreas, and an increase in a number of pancreatic β cells in the pancreas.

2. The device or system of claim 1, wherein the signal stimulates the neural activity of the pancreas-related sympathetic nerve.

3. The device or system of claim 1, wherein the signal generator is a voltage or current source configured to generate an electrical signal to be applied to the pancreas-related sympathetic nerve via the at least one electrode.

4. The device or system of claim 3, wherein the at least one electrode is a cuff electrode.

5. The device or system of claim 4, wherein the cuff electrode is an electrode array configured to stimulate the pancreas-related sympathetic nerve in a selective manner.

6. The device or system of claim 3, wherein the signal selectively stimulates neural activity of nerve fibers supplying the lymphatic system of the pancreas.

7. The device or system of claim 3, wherein the electrical signal has a frequency between 0.1 Hz and 100 Hz.

8. The device or system of claim 3, wherein the electrical signal has a current between 0.01 mA and 10 mA.

9. The device or system of claim 3, wherein the electrical signal is a charge-balanced DC signal comprising a cathodic pulse and an anodic pulse.

10. The device or system of claim 1, wherein the reduction in inflammation systemically is indicated by levels of circulating cytokines.

11. The device or system of claim 1, wherein the reduction in inflammation systemically is indicated by levels of C reactive protein.

12. The device or system of claim 1, wherein the reduction in inflammation locally in the pancreas is indicated by levels of C-peptide.

13. The device or system of claim 1, wherein the reduction in inflammation locally in the pancreas is indicated by levels of autoreactive T cells.

14. The device or system of claim 1, wherein the reduction in inflammation locally in the pancreas is indicated by levels of autoantibodies.

15. The device or system of claim 1, comprising a detector for detecting one or more signals indicative of one or more physiological parameters; determining from the one or more signals one or more physiological parameters; determining the one or more physiological parameters indicative of worsening of the physiological parameter; and causing the signal to be applied to the pancreas-related sympathetic nerve via the at least one electrode.

16. The device or system of claim 1, wherein the signal generator is configured to apply the electric signal for a finite period of time.

17. A method of reversibly modulating neural activity in a pancreas-related sympathetic nerve, comprising: (i) implanting in the subject a device or system of claim 1; (ii) positioning the neural interfacing element in signaling contact with the pancreas-related sympathetic nerve; and optionally (iii) activating the device or system.

18. The method of claim 17, wherein the method is for treating type 1 diabetes (T1D).

19. The method of claim 17, further comprising administering GABA, a GABA analogue, or a GABA-enhancing agent to the subject.

20. The method of claim 19, wherein the GABA-enhancing agent is selected from the group consisting of benzodiazepines; barbiturates; baclofen; acamprosate; pregabalin; gabapentin; tiagabine; lamotrigine; topiramate; neuroactive steroids; nabiximols; and combinations thereof.

* * * * *

UNITED STATES PATENT AND TRADEMARK OFFICE
CERTIFICATE OF CORRECTION

| | | |
|---|---|---|
| PATENT NO. | : 11,517,754 B2 | Page 1 of 1 |
| APPLICATION NO. | : 16/610658 | |
| DATED | : December 6, 2022 | |
| INVENTOR(S) | : Sridhar et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 211 days.

Signed and Sealed this
Fourteenth Day of January, 2025

Derrick Brent
*Acting Director of the United States Patent and Trademark Office*